United States Patent
Murphy et al.

(10) Patent No.: US 6,994,093 B2
(45) Date of Patent: Feb. 7, 2006

(54) VENTRICULAR RESTORATION SHAPING APPARATUS AND METHOD OF USE

(75) Inventors: Gregory Murphy, Richardson, TX (US); Mitta Suresh, Richardson, TX (US); Albert Davis, Richardson, TX (US)

(73) Assignee: Chase Medical, L.P., Richardson, TX (US)

( * ) Notice: Subject to any disclaimer, the term of this patent is extended or adjusted under 35 U.S.C. 154(b) by 179 days.

(21) Appl. No.: 09/864,510

(22) Filed: May 24, 2001

(65) Prior Publication Data

US 2002/0133143 A1    Sep. 19, 2002

Related U.S. Application Data

(60) Provisional application No. 60/272,073, filed on Feb. 28, 2001.

(51) Int. Cl.
*A61B 19/00* (2006.01)
*A61F 2/02* (2006.01)

(52) U.S. Cl. ................. 128/898; 600/16; 600/587; 623/3.1; 33/512

(58) Field of Classification Search ............... 606/151; 128/898; 600/16, 37, 587; 623/3.1; 33/512
See application file for complete search history.

(56) References Cited

U.S. PATENT DOCUMENTS

| | | |
|---|---|---|
| 2,701,559 A | 2/1955 | Cooper |
| 3,568,659 A | 3/1971 | Karnegis |
| 3,874,388 A | 4/1975 | King et al. |
| 3,983,863 A | 10/1976 | Janke et al. |
| 4,685,446 A | 8/1987 | Choy |
| 4,690,134 A | 9/1987 | Snyders |
| 4,771,765 A | 9/1988 | Choy et al. |
| 4,785,795 A | 11/1988 | Singh |
| 4,817,637 A * | 4/1989 | Hillegass et al. ........... 128/899 |
| 4,821,723 A | 4/1989 | Baker, Jr. et al. |
| 4,861,330 A | 8/1989 | Voss |

(Continued)

FOREIGN PATENT DOCUMENTS

DE        29911694        8/1999

(Continued)

OTHER PUBLICATIONS

Marisa Di Donato et al., "Effects of the Dor Procedure on Left Ventricular Dimension and Shape and Geometric Correlates of Mitral Regurgitation One year After Surgery", The Journal of Thoracic and Cardiovascular Surgery, Jan. 2001, pp. 91-96.

(Continued)

*Primary Examiner*—Ralph A. Lewis
(74) *Attorney, Agent, or Firm*—Meyertons, Hood, Kivlin, Kowert & Goetzel, P.C.; Eric B. Meyertons

(57) ABSTRACT

Apparatuses and methods are provided to reconstruct an enlarged left ventricle of a human heart, using a shaper, having a size and shape substantially equal to the size and shape of an appropriate left ventricle, wherein the shaper is adapted to be temporarily placed into the enlarged left ventricle during a surgical procedure. Another embodiment comprises a ventricular patch adapted for placement into the left ventricle of a heart made from a sheet of biocompatible material, and having a plurality of markings coupled to the sheet, wherein the markings are configured in distinct patterns for post operatively evaluating movement of the patch. In another aspect of one embodiment, a device is presented, comprising of a handle and a sizing template adapted to be coupled to the handle. Such components are also presented as a kit for use during ventricular restoration surgery.

145 Claims, 10 Drawing Sheets

U.S. PATENT DOCUMENTS

| | | | |
|---|---|---|---|
| 4,902,273 A | 2/1990 | Choy et al. | |
| 4,917,089 A | 4/1990 | Sideris | |
| 4,938,231 A | 7/1990 | Milijasevic et al. | |
| 4,957,477 A | 9/1990 | Lundback | |
| 4,973,300 A | 11/1990 | Wright | |
| 5,041,130 A | 8/1991 | Cosgrove et al. | |
| 5,089,005 A | 2/1992 | Harada | |
| 5,131,905 A | 7/1992 | Grooters | |
| 5,139,517 A | 8/1992 | Corral | |
| 5,167,628 A | 12/1992 | Boyles | |
| 5,169,378 A * | 12/1992 | Figuera | 600/16 |
| 5,171,299 A | 12/1992 | Heitzmann et al. | |
| 5,176,619 A | 1/1993 | Segalowitz | |
| 5,192,314 A | 3/1993 | Daskalakis | |
| 5,255,678 A * | 10/1993 | Deslauriers et al. | |
| 5,258,000 A | 11/1993 | Gianturco | |
| 5,334,146 A | 8/1994 | Ozasa | |
| 5,409,000 A * | 4/1995 | Imran | |
| 5,411,527 A | 5/1995 | Alt | |
| 5,425,744 A | 6/1995 | Fagan et al. | |
| 5,433,727 A | 7/1995 | Sideris | |
| 5,451,235 A | 9/1995 | Lock et al. | |
| 5,465,717 A * | 11/1995 | Imran et al. | |
| 5,489,296 A | 2/1996 | Love et al. | |
| 5,507,811 A | 4/1996 | Koike et al. | |
| 5,509,428 A | 4/1996 | Dunlop | |
| 5,526,810 A * | 6/1996 | Wang | |
| 5,603,337 A | 2/1997 | Jarvik | |
| 5,609,157 A * | 3/1997 | Panescu et al. | |
| 5,632,776 A | 5/1997 | Kurumatani et al. | |
| 5,702,343 A | 12/1997 | Alferness | |
| 5,722,401 A * | 3/1998 | Pietroski et al. | |
| 5,725,552 A | 3/1998 | Kotula et al. | |
| 5,738,626 A | 4/1998 | Jarvik | |
| 5,749,839 A * | 5/1998 | Kovacs | 601/153 |
| 5,797,960 A | 8/1998 | Stevens et al. | |
| 5,800,528 A | 9/1998 | Lederman et al. | |
| 5,814,098 A | 9/1998 | Hinnenkamp et al. | |
| 5,843,177 A | 12/1998 | Vanney et al. | |
| 5,846,260 A | 12/1998 | Maahs | |
| 5,846,261 A | 12/1998 | Kotula et al. | |
| 5,868,779 A | 2/1999 | Ruiz | |
| 5,885,228 A | 3/1999 | Rosenman et al. | |
| 5,904,680 A | 5/1999 | Kordis et al. | |
| 5,908,445 A * | 6/1999 | Whayne et al. | 607/122 |
| 5,921,935 A | 7/1999 | Hickey | |
| 5,923,770 A | 7/1999 | O'Donnell et al. | |
| 5,944,738 A | 8/1999 | Amplatz et al. | |
| 5,951,543 A | 9/1999 | Brauer | |
| 5,957,977 A | 9/1999 | Melvin | |
| 5,964,806 A * | 10/1999 | Cook et al. | 623/11.11 |
| 5,971,911 A | 10/1999 | Wilk | |
| 6,004,329 A | 12/1999 | Myers et al. | |
| 6,019,739 A | 2/2000 | Rhee et al. | |
| 6,024,096 A | 2/2000 | Buckberg | |
| 6,099,832 A | 8/2000 | Mickle et al. | |
| 6,109,852 A | 8/2000 | Shahinpoor et al. | |
| 6,123,715 A | 9/2000 | Amplatz | |
| 6,125,852 A | 10/2000 | Stevens et al. | |
| 6,143,012 A | 11/2000 | Gausepohl | |
| 6,152,144 A | 11/2000 | Lesh et al. | |
| 6,162,168 A | 12/2000 | Schweich, Jr. et al. | |
| 6,162,537 A | 12/2000 | Martin et al. | |
| 6,179,791 B1 | 1/2001 | Krueger | |
| 6,183,411 B1 | 2/2001 | Mortier et al. | |
| 6,205,411 B1 | 3/2001 | DiGioia, III et al. | |
| 6,210,338 B1 * | 4/2001 | Afremov et al. | 600/481 |
| 6,216,043 B1 * | 4/2001 | Swanson et al. | 607/122 |
| 6,221,104 B1 | 4/2001 | Buckberg et al. | |
| 6,231,601 B1 | 5/2001 | Myers et al. | |
| 6,261,832 B1 | 7/2001 | Law | |
| 6,322,588 B1 | 11/2001 | Ogle et al. | |
| 6,350,281 B1 | 2/2002 | Rhee et al. | |
| 6,360,749 B1 | 3/2002 | Jayaraman | |
| 6,366,684 B1 | 4/2002 | Gerard et al. | |
| 6,368,356 B1 | 4/2002 | Zhong et al. | |
| 6,406,420 B1 | 6/2002 | McCarthy et al. | |
| 6,419,669 B1 | 7/2002 | Frazier et al. | |
| 6,439,237 B1 * | 8/2002 | Buckberg et al. | 128/898 |
| 6,450,171 B1 * | 9/2002 | Buckberg et al. | 128/898 |
| 6,544,167 B2 | 4/2003 | Buckberg et al. | |
| 6,551,303 B1 | 4/2003 | Van Tassel et al. | |
| 6,652,556 B1 | 11/2003 | Van Tassel et al. | |
| 6,681,773 B2 * | 1/2004 | Murphy et al. | 128/898 |
| 6,702,763 B2 | 3/2004 | Murphy et al. | |
| 6,726,696 B1 | 4/2004 | Houser et al. | |
| 6,852,076 B2 | 2/2005 | Nikolic et al. | |
| 6,887,192 B1 | 5/2005 | Whayne et al. | |
| 2002/0026092 A1 | 2/2002 | Buckberg et al. | |
| 2002/0029783 A1 | 3/2002 | Stevens et al. | |
| 2002/0056461 A1 | 5/2002 | Jayaraman | |
| 2002/0133227 A1 | 9/2002 | Murphy et al. | |
| 2002/0198603 A1 | 12/2002 | Buckberg et al. | |
| 2003/0045896 A1 | 3/2003 | Murphy et al. | |
| 2003/0050659 A1 | 3/2003 | Murphy et al. | |
| 2003/0050682 A1 | 3/2003 | Sharkey et al. | |
| 2003/0050685 A1 | 3/2003 | Nikolic et al. | |
| 2003/0060674 A1 | 3/2003 | Gifford, III et al. | |
| 2003/0105384 A1 | 6/2003 | Sharkey et al. | |
| 2003/0109770 A1 | 6/2003 | Sharkey et al. | |
| 2003/0158570 A1 | 8/2003 | Ferrazzi | |
| 2003/0163191 A1 | 8/2003 | Nikolic et al. | |
| 2003/0181940 A1 | 9/2003 | Murphy et al. | |
| 2003/0192561 A1 | 10/2003 | Murphy et al. | |
| 2004/0243170 A1 | 12/2004 | Murphy et al. | |
| 2004/0249408 A1 | 12/2004 | Murphy et al. | |
| 2005/0096498 A1 | 5/2005 | Houser et al. | |

FOREIGN PATENT DOCUMENTS

| | | |
|---|---|---|
| RU | 2107467 | 3/1998 |
| WO | 95/18593 | 7/1995 |
| WO | 99/03973 | 1/1999 |
| WO | WO 99/56655 | 11/1999 |
| WO | 02/19917 A1 | 3/2002 |
| WO | 02/094136 A1 | 11/2002 |

OTHER PUBLICATIONS

Hisayoshi Suma et al., "Nontransplant Cardiac Surgery For End-Stage Cardiomyopathy", The Journal of Thoracic and Cardiovascular Surgery, Jun. 2000, pp. 1233-1245.

Rufus Baretti et al., "Batista Procedure: Elliptical Modeling Against Spherical Distention", European Journal of Cardio-Thoracic Surgery 17, 2000, pp. 52-57.

Randas Batista, "Partial Left Ventriculectomy—The Batista Procedure", European Journal of Cardio-Thoracic Surgery 15, 1999, pp. S12-S19.

Gerald D. Buckberg, M.D., "Commonality of Ischemic and Dilated Cardiomyopathy: Laplace and Ventricular Restoration", The UCLA Medical Center, Department of Surgery, Los Angeles, California, 1999, pp. 53-59.

F. Fantini et al., "Effects of Reconstructive Surgery For Left Ventricular Anterior Aneurysm on Ventriculoarterial Coupling", Heart 1999, 81, pp. 171-176.

V. Dor et al., "Endoventricular Patch Reconstruction in Large Ischemic Wall-Motion Abnormalities", The Centre Cardio-Thoracique, Monaco, 1999, pp. 46-52.

Randall C. Starling and Patrick M. McCarthy, "Partial Left Ventriculectomy: Sunrise or Sunset?", European Journal of Heart Failure, 1999, pp. 313-317.

V. Dor et al., "Endoventricular Patch Plasty for Large L.V. Akinesia" Video tape from Centre de Cardio-Thoracique de Monaco, Sep. 1998.

Gerald D. Buckberg, MD, "Surgery for Adult Cardiovascular Disease: Editorial: Defining the Relationship Between Akinesia and Dyskinesia and the Cause of Left Ventricular Failure After Anterior Infraction and Reversal of Remodeling to Restoration", 1998, pp. 47-49.

Sakamoto et al., "Restoring the Remodeled Enlarged Left Ventricle: Experimental Benefits of In Vivo Porcine Cardioreduction in the Beating Open Heart", Department of Cardiology, UCLA School of Medicine, 1998, pp. 429-439.

Athanasuleas, MD et al., "Restoration of Contractile Function in the Enlarged Left Ventricle by Exclusion of Remodeled Akinetic Anterior Segment: Surgical Strategy, Myocardial Protection, and Angiographic Results", Journal of Cardiovascular Surgery, 1998, pp. 418-428.

V. Dor, MD et al., "Endoventricular Patch Plasties with Septal Exclusion for Repair of Ischemic Left Ventricle: Technique, Results and Indications from A Series of 781 Cases", The Japanese Journal of Thoracic and Cardiovascular Surgery, 1998, pp. 389-398.

V. Dor, MD et al., "Ventricular Remodeling in Coronary Artery Disease", Centre Cardio-Thoracique de Monaco, 1997, pp. 533-537.

Di Donato, MD et al., "Akinetic Versus Dyskinetic Postinfarction Scar: Relation to Surgical Outcome in Patients Undergoing Endoventricular Circular Patch Plasty Repair" American College of Cardiology, vol. 29, 1997, pp. 1569-1575.

Vincent Dor, "The Treatment of Refractory Ischemic Ventricular Tachycardia by Endoventricular Patch Plasty Reconstruction of the Left Ventricle", Seminars in Thoracic and Cardiovascular Surgery, vol. 2, No 2, Apr., 1997, pp. 146-155.

Vincent Dor, "Reconstructive left Ventricular Surgery for Post-Ischemic Akinetic Dilatation", Seminars in Thoracic and Cardiovascular Surgery, vol. 2, No. 2, Apr., 1997, pp. 139-145.

Vincent Dor, "Left Ventricular Aneurysms: The Endoventricular Circular Patch Plasty", Seminars in Thoracic and Cardiovascular Surgery, vol. 9, No. 2, Apr., 1997, pp. 123-130.

James L. Cox, "Surgical Management of Left Ventricular Aneurysms: A Clarification of the Similarities and Differences Between the Jatene and Dor Techniques", Seminars in Thoracic and Cardiovascular Surgery, vol. 9, No. 2, Apr., 1997, pp. 131-138.

Di Donato et al., "Outcome of Left Ventricular Aneurysmectomy with Patch Repair in Patients with Severely Depressed Pump Function", The American Journal of Cardiology, vol. 76, Sep. 15, 1995, pp. 557-561.

V. Dor et al., Surgery For Acquired Heart Disease, Late Hemodynamic Results After Left Ventricular Patch Repair Associated with Coronary Grafting in Patients with Postinfarction Akinetic or Dyskinetic Aneurysm of the Left Ventricle, The Journal of Thoracic and Cardiovascular Surgery, Nov. 1995, pp. 1291-1301.

Elefteriades et al., "Left Ventricular Aneurysmectomy in Advanced Left Ventricular Dysfunction", Cardiology Clinics, vol. 13, No. 1, Feb. 1995, pp. 59-72.

V. Dor et al., "Left Ventricular Shape Changes Induced by Aneurysmectomy with Endoventricular Circular Patch Plasty Reconstruction", The European Society of Cardiology, 1994, pp. 1063-1069.

Cooley, MD et al., "Intracavitary Repair of Ventricular Aneurysm and Regional Dyskinesia", Departments of Cardiovascular Surgery and Cardiology, Texas Heart Institute, Houston, TX., Jan. 1992, pp. 417-242.

Di Donato et al., "Early Hemodynamic Results of Left Ventricular Reconstructive Surgery for Anterior Walls Left Ventricular Aneurysm", The American Journal of Cardiology, vol. 69, Apr. 1, 1992, pp. 886-890.

Francis Fontan, MD, "Transplantation of Knowledge", The Journal of Thoracic and Cardiovascular Surgery, 1990, pp. 387-395.

Denton A. Cooley, MD, "Ventricular Endoaneurysmorrhaphy: A Simplified Repair for Extensive Postinfarction Aneurysm", Journal of Cardiac Surgery, vol. 4, No. 3, 1989, pp. 200-205.

V. Dor et al., "Left Ventricular Aneurysm: A New Surgical Approach", Thorac.Cardiovasc.Surgery37, Jun. 16, 1988, pp. 11-19.

T. Shiga et al. "Deformation of Polyelectrolyte Gels under the Influence of Electric Field" *Journal of Applied Polymer Science*, 1990,39, 2305.

J. Bohm et al. "Endoventricular Patch Plasty for Restoration of Ventricular Geometry and Pump Function in Ventricular Aneurysm" *Z. Kardiol*, 1996, 85, Supplement No. 4, 43-46.

Di Donato et al., "Early Hemodynamic Results of Left Ventricular Reconstructive Surgery for Anterior Wall Left Ventricular Aneurysm" *The American Journal of Cardiology*, 1992, 69, 886-890.

V. Dor, "Left Ventricular Aneurysms: The Endoventricular Circular Patch Plasty" *Seminars in Thoracic and Cardiovascular Surgery*, 1997, 9, No. 2, 123-130.

V. Dor et al., "Ventricular remodeling in coronary artery disease" *Current Opinion in Cardiology*, Centre Cardio-Thoracique de Monaco, 1997, 12, 533-537.

A. D. Jatene, "Left Ventricular aneurysmectomy: Resection or reconstruction" *The Journal of Thoracic and Cardiovascular Surgery*, 1985, 89, 321-331.

K. Emmrich, "Contribution to the Discussion of the Lecture by J. Bohm, Berlin" *Z. Kardiol*, 1996, 85, Supplement No. 4, 47-48.

V. Dor, "Recontructive Left Ventricular Surgery for Post-Ischemic Akinetic Dilatation" *Seminars in Thoracic Surgery*, 1997, 9, No. 2, 139-145.

T. Kono et al., "Left Ventricular Shape Is the Primary Determinant of Functional Mitral Regurgitation in Heart Failure" *JACC*, Dec. 1992, vol. 20, No. 7, p. 1594-1598.

G. E. Burch et al., "Angle of traction of the papillary muscle in normal and dilated hearts: A theoretic analysis of its importance in mitral valve dynamics" *American Heart Journal*, Jul. 1972, vol. 84, No. 1, p. 141-144.

R. E. Michler et al., "Minimally Invasive Mitral Valve Replacement and Multivessel Coronary Artery Bypass Through a Limited Right Lateral Thoracotomy using a Balloon Aortic Cannula" *The Heart Surgery Forum*, 2001, vol. 5, No. 1, p. 49-51.

V. Dor, "Left ventricular restoration by endoventricular circular patch plasty (EVCPP)" *Z. Kardiol*, 2000, vol. 89, Suppl. 7, p. VII/70-VII/75.

V. Dor et al., "Endoventricular Patch Reconstruction in Large Ischemic Wall-Motion Abnormalities" *J. Card Surg*, 1999, 14, 46-52.

Office Action for U.S. Appl. No. 10/454,978 mailed Sep. 27, 2004.

International Search Report and Written Opinion for PCT/US04/06061 mailed Oct. 8, 2004.

International Preliminary Examination Report for PCT/02/16304 mailed Jul. 15, 2004.

International Search Report for EP 02729297 mailed May 19, 2004.

Di Donato, M. et al. "Regional Myocardial performance of non-ischaemic zones remote from anterior wall left ventricular aneurysm—Effects of aneurysmectomy", European Heart Journal, (1995) 16, 1285-1292.

Written Opinion for PCT/US/02/16304 mailed May 27, 2003.

International Preliminary Examination Report for PCT/US02/16304 mailed Mar. 29, 2005.

International Preliminary Examination Report for PCT/US04/06061 mailed Apr. 1, 2005.

International Search Report for PCT/US02/16304 mailed Aug. 22, 2002.

G. D. Buckberg, "Congestive heart Failure: Treat the Disease, Not the Symptom—Return to Normalcy" J Thorac Cardiovasc Surg, Apr., 2001, vol. 121, No. 4, pp. 628-637.

C. L. Anthanasuleas et al., "Surgical Anterior Ventricular Endocardial Restoration (SAVER) in the Dilated Remodeled Ventricle After Anterior Myocardial Infarction" Journal of the American College of Cardiology, Apr., 2001, vol. 37, No. 5, pp. 1199-1209.

Pending claims for U.S. Appl. No.: 10/454,978, published as Publication No.: 20030192561.

Pending claim set for a recently filed (Apr. 25, 2005, Continuation of U.S. Appl. No.: 10/454,978, published as Publication No.: 20030192561.

Pending claim set for U.S. Appl. No.: 09/864,793, published as Publication No.: 20020133227.

Pending claim set for U.S. Appl. No. 10/350,297, published as Publication No.:200301811940

Pending claim set and specification for U.S. Appl. No. 10/502,740.

Pending claim set and specification for U.S. Appl. No. 10/164,146.

Pending claims for U.S. Appl. No. 10/235,295, published as Publication No. 20040249408.

Pending claim set for U.S. Appl. No. 10/235,295, published as Publication No. 20040243170.

Pending claim set and specification for U.S. Appl. No. 11/032,514.

* cited by examiner

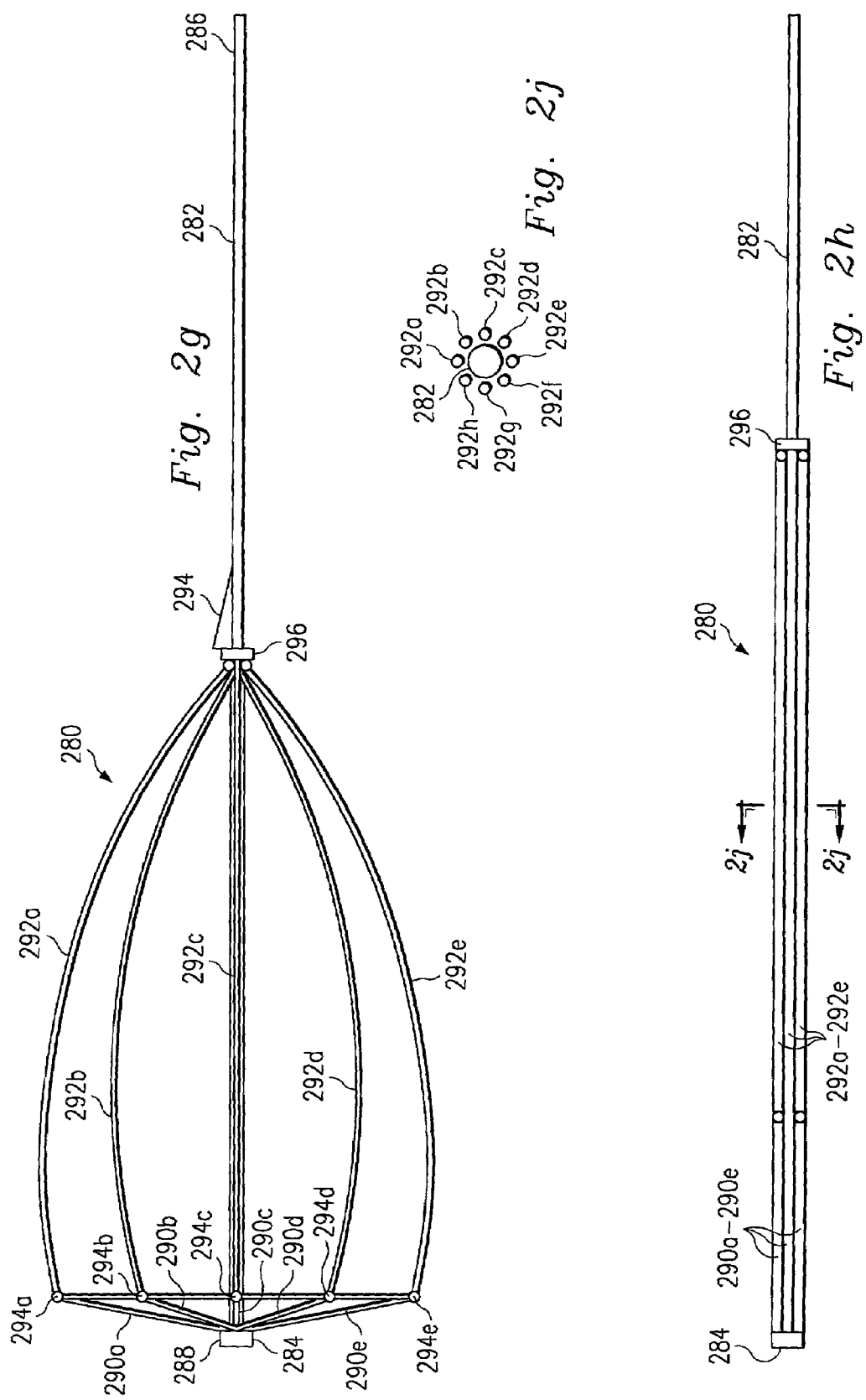

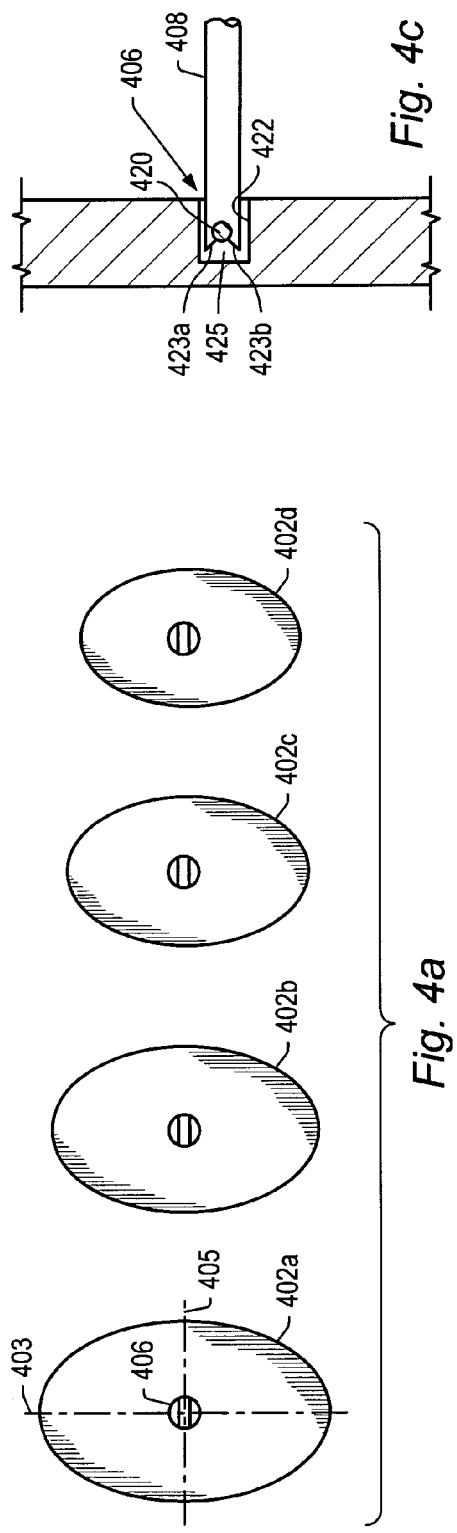
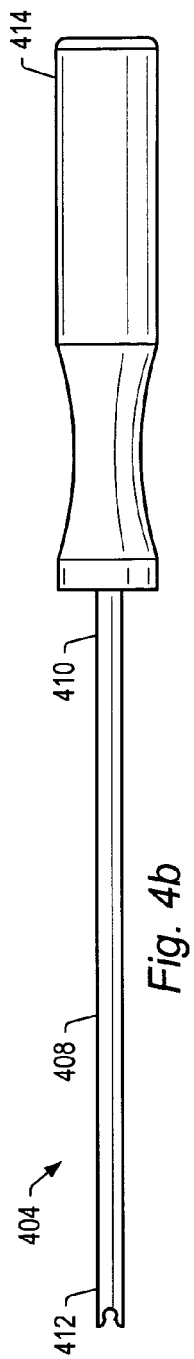
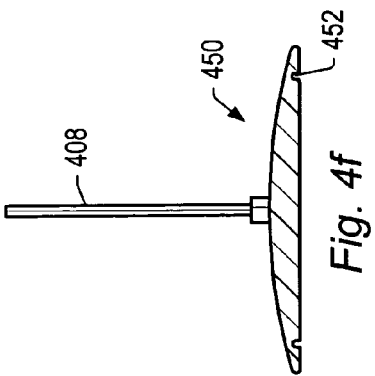
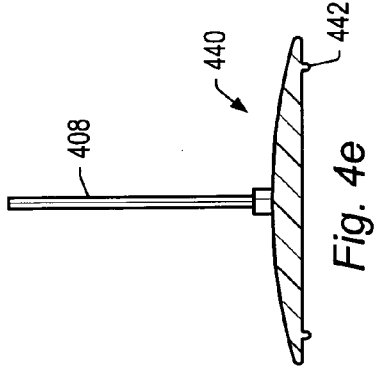
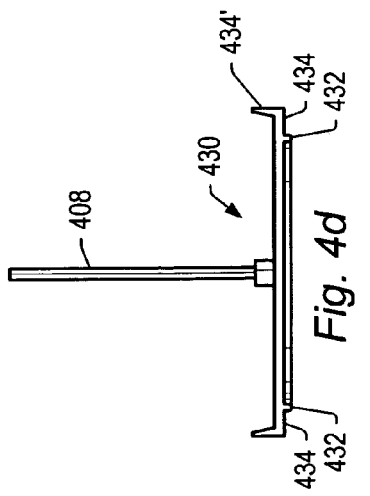

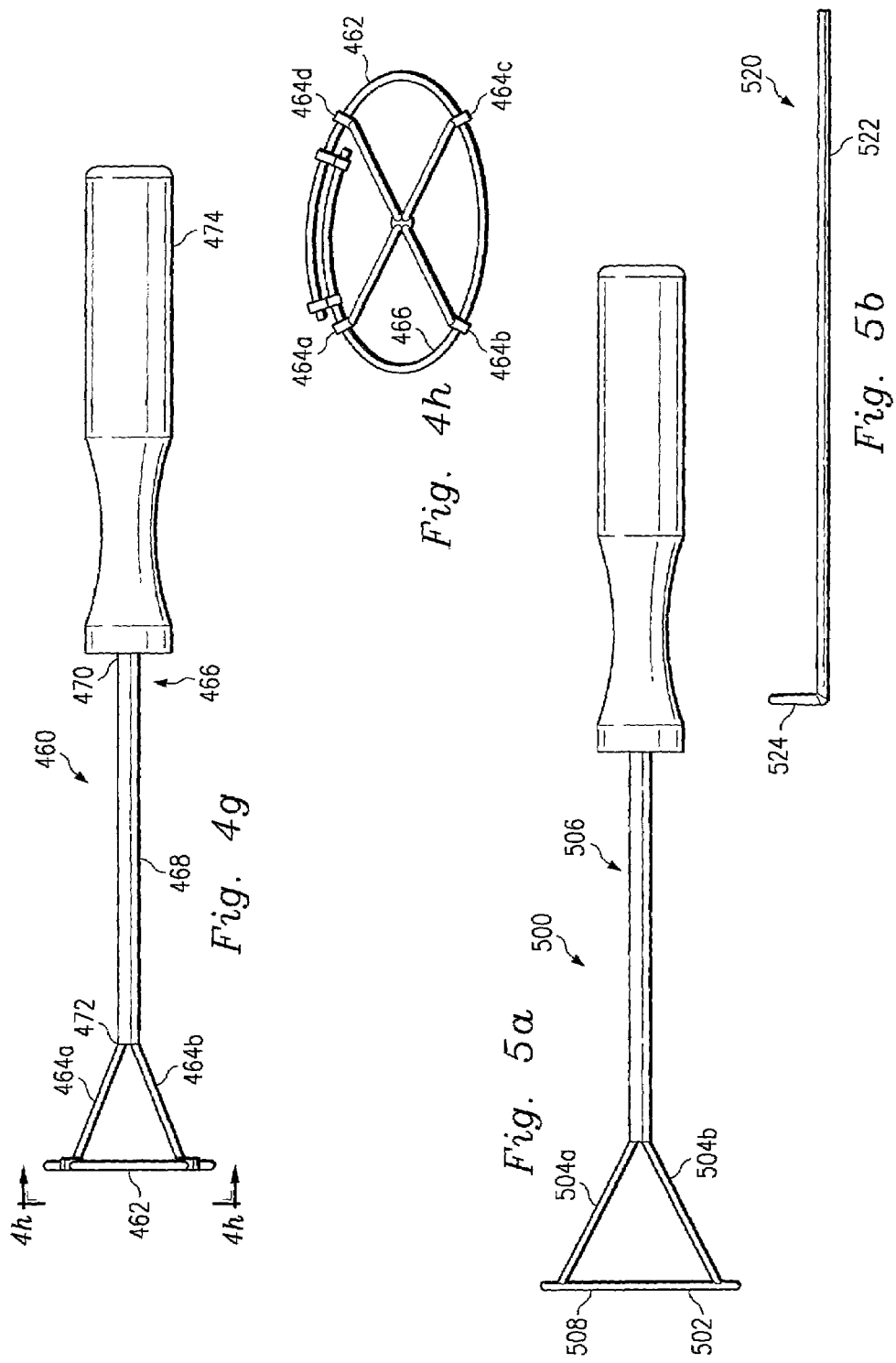

VENTRICULAR RESTORATION SHAPING APPARATUS AND METHOD OF USE

CROSS-REFERENCE

This invention claims the benefit of U.S. Provisional Application Ser. No. 60/272,073 filed on Feb. 28, 2001 and is also related to U.S. application Ser. No. 09/864,503 now U.S. Pat. No. 6,702,763, Ser. No. 09/864,793, and Ser. No. 09/864,794 now U.S. Pat. No. 6,681,773, all of which were filed on May 24, 2001.

TECHNICAL FIELD

This invention relates generally to surgical methods and apparatus for addressing cardiomyopathy, and more specifically to methods and apparatus for restoring the architecture and normal function of a mammalian heart.

BACKGROUND

The function of a heart in an animal is primarily to deliver life-supporting oxygenated blood to tissue throughout the body. This function is accomplished in four stages, each relating to a particular chamber of the heart. Initially deoxygenated blood is received in the right auricle of the heart. This deoxygenated blood is pumped by the right ventricle of the heart to the lungs where the blood is oxygenated. The oxygenated blood is initially received in the left auricle of the heart and ultimately pumped by the left ventricle of the heart throughout the body. It can be seen that the left ventricular chamber of the heart is of particular importance in this process as it is relied upon to pump the oxygenated blood initially through an aortic valve into and ultimately throughout the entire vascular system.

The amount of blood pumped from the left ventricle divided by the amount of blood available to be pumped is referred to as the ejection fraction of the heart. Generally, the higher the ejection fraction the more healthy the heart. A normal heart, for example may have a total volume of one hundred milliliters and an ejection fraction of 60 percent. Under these circumstances, 60 milliliters of blood are pumped with each beat of the heart. It is this volume in the normal heart of this example that is pumped with each beat to provide nutrients including oxygen to the muscles and other tissues of the body.

The heart is part of the body tissue, and the heart muscle also requires oxygenated blood. Its normal function is greatly upset by clotting or closure of the coronary arteries. When the coronary arteries are blocked, an associate portion of the heart muscle becomes oxygen-starved and begins to die. This is clinically referred to as a heart attack. Ischemic cardiomyopathy typically occurs as the rest of the heart dilates in an attempt to maintain the heart's output to the body.

As the ischemia progresses through its various stages, the affected myocardium dies losing its ability to contribute to the pumping action of the heart. The ischemic muscle is no longer capable of contracting so it cannot contribute to either squeezing or twisting motion required to pump blood. This non-contracting tissue is said to be "akinetic." In severe cases the akinetic tissue, which is not capable of contracting, is elastic so that blood pressure tends to develop a bulge or expansion of the chamber. In this situation, this muscle tissue is not only akinetic, in that it does not contribute to the pumping function, but it is in fact "dyskinetic," in that it detracts from the pumping function. This situation is particularly detrimental as the heart loses even more of its energy due to pumping the blood to the bulge instead of through the aorta.

After a heart attack, the body seems to realize that with a reduced pumping capacity, the ejection fraction of the heart is automatically reduced. For example, the ejection fraction may drop from a normal 60 percent to 20 percent. Realizing that the body still requires the same volume of blood for oxygen and nutrition, the body causes its heart to dilate or enlarge in size so that the smaller ejection fraction pumps about the same amount of blood. As noted, a normal heart with a blood capacity of seventy milliliters and an ejection fraction of 60 percent would pump approximately 42 milliliters per beat. The body seems to appreciate that this same volume per beat can be maintained by an ejection fraction of only 30 percent if the ventricle enlarges to a capacity of 140 milliliters. This increase in volume, commonly referred to as "remodeling", not only changes the volume of the left ventricle, but also its shape. The heart becomes greatly enlarged. An enlarged heart will tend to change its architecture from the normal conical or apical shape, to a generally spherical shape.

On the level of the muscle fibers, it has been noted that enlargement or dilation of the heart causes the fibers to reorient themselves so that they are directed away from the inner heart chamber containing the blood. As a consequence, the fibers are poorly oriented to accomplish even the squeezing action, as the lines of force become less perpendicular to the heart wall. This change in fiber orientation occurs as the heart dilates and moves from its normal elliptical shape to its dilated spherical shape. The spherical shape further reduces pumping efficiency since the fibers which normally encircle the apex to facilitate writhing are changed to a more flattened formation as a result of these spherical configurations. The resulting orientation of these fibers produces lines of force, which are also directed laterally of the ventricle chamber. Thus, the dilation and resulting spherical configuration greatly reduces contraction efficiency.

Perhaps the most notable symptom of ischemic cardiomyopathy is the reduction in the ejection fraction which may diminish, for example, from a normal 60 percent to only 20 percent. This results clinically in fatigue and in an inability to do stressful activities that require an increase in output of blood from the heart. The output of blood by the enlarged heart at rest is kept normal, but the capacity to increase output of blood during stress (i.e., exercise, walking) is significantly reduced. Of course, the change in architecture has a dramatic effect on wall thickness, radius, and stress on the heart wall. In particular, it will be noted that absent the normal conical shape, the twisting motion of the heart, which can account for as much as one half of the pumping action, is lost. As a consequence, the more spherical architecture must rely almost totally on the lateral squeezing action to pump blood. This lateral squeezing action is inefficient and very different from the more efficient twisting action of the heart. The change in architecture of the heart will also typically change the structure and ability of the mitral valve to perform its function in the pumping process. Valvular insufficiency can also occur due to dilatation.

Although the dilated heart may be capable of sustaining life, it is significantly stressed and rapidly approaches a stage where it can no longer pump blood effectively. In this stage, commonly referred to as congestive heart failure, the heart becomes distended and is generally incapable of pumping blood returning from the lungs. This further results in lung congestion and fatigue. Congestive heart failure is a major cause of death and disability in the United States with approximately 400,000 new cases annually.

Following coronary occlusion, successful acute reperfusion by thrombolysis, (clot dissolution) percutaneous angioplasty, or urgent surgery can decrease early mortality by reducing arrhythmias and cardiogenic shock. It is also known that addressing ischemic cardiomyopathy in the acute phase, for example with reperfusion, may salvage the epicardial surface. Although the myocardium may be rendered akinetic, at least it is not dyskinetic. Post-infarction surgical re-vascularation can be directed at remote viable muscle to reduce ischemia. However, it does not address the anatomical consequences of the akinetic region of the heart that is scarred. Despite these techniques for monitoring ischemia, cardiac dilation and subsequent heart failure continue to occur in approximately 50 percent of post-infraction patients discharged from the hospital.

Various surgical approaches have been tried to treat the dilation of the ventricle by primarily reducing the ventricular volume. Some of these procedures involve removing or excluding dyskinetic and akinetic regions of the heart, then surgically joining the viable portions of the myocardial walls, typically with the use of a patch surgically placed in the walls using a Fontan stitch.

Typically, the exact placement of the patch has been visually determined using only a visual indication where the typically white scar tissue meets the typically red normal tissue. Location of the patch has been facilitated in a further procedure where a continuous suture has been placed around the ventricular wall to define a neck for receiving the patch. The neck has been formed in the white scar tissue rather than the soft viable muscle. This procedure has relied on cardioplegia methods to stop the beating of the heart and to aid in suture placement.

These surgical procedures have been met with some success as the ejection fraction has been increased, for example, from 24 percent to 42 percent. However, despite this level of success, it is often difficult for the surgeon to reconstruct the shape and size of the left ventricle. If the reconstructed ventricle is too small, the patient will not be able to pump enough oxygenated blood. If the reconstructed ventricle is too large, the ejection fraction may diminish. In addition to the size, the shape of the reconstructed ventricle is also important. If the left ventricle is reconstructed in a spherical shape, a twisting motion of the heart about its apex, which can account for as much as one half of the pumping action, is lost. As a consequence, the spherical shaped reconstructed ventricle must rely almost totally on the lateral squeezing action to pump blood. This lateral squeezing action is inefficient and very different from the more efficient twisting action of the heart. What is needed, therefore is a reliable method and apparatus to allow a surgeon to reconstruct the left ventricle to the appropriate shape, size and contour.

SUMMARY

In response to these and other problems, an improved apparatus and method is provided for restoring the geometry of the left ventricle to counteract the effects of cardiac remodeling. One embodiment of the present invention provides an apparatus and method to reconstruct an enlarged left ventricle of a human heart, using a shaper, having a size and shape substantially equal to the size and shape of an appropriate left ventricle, wherein the shaper is adapted to be temporarily placed into the enlarged left ventricle during a surgical procedure. Another aspect of one embodiment comprises a ventricular patch adapted for placement into the left ventricle of a heart made from a sheet of biocompatible material, and having a plurality of markings coupled to the sheet, wherein the markings are configured in distinct patterns for post operatively evaluating movement of the patch. In another aspect of one embodiment, a device is presented, comprising a handle and a sizing template adapted to be coupled to the handle. Such components are also presented as a kit for use during ventricular restoration surgery.

BRIEF DESCRIPTION OF THE FIGURES

FIG. 2g is a side view of a wire frame embodiment of a shaping device in an expanded condition.

FIG. 2h is a side view of a wire frame embodiment of a shaping device in a collapsed condition.

FIG. 2j is a section view cut transversely through the embodiment of FIG. 2h.

FIG. 3b is a top view of one embodiment of markings which may be coupled to the patch of FIG. 3a.

FIG. 3c is a top view of one embodiment of markings which may be coupled to the patch of FIG. 3a.

FIG. 3d is a top view of one embodiment of markings which may be coupled to the patch of FIG. 3a.

FIG. 3e is a top view of one embodiment of markings which may be coupled to the patch of FIG. 3a.

FIG. 4a is a top view of one embodiment of a set of sizers.

FIG. 4b is a top view of one embodiment of a handle to be used with the set of sizers illustrated in FIG. 4a.

FIG. 4c is a detailed section view illustrating a connection between the handle and a sizer.

FIG. 4d is a section view of one embodiment of a sizer.

FIG. 4e is a section view of one embodiment of a sizer.

FIG. 4f is a section view of one embodiment of a sizer.

FIG. 4g is a top view of one embodiment of a sizer made of malleable wire.

FIG. 4h is a side view of the sizer illustrated in FIG. 4g.

FIG. 5a is a top view of one embodiment of a patch holder.

FIG. 5b is a top view of one embodiment of a suture hook.

FIG. 7b is a continuation of the process illustrated in FIG. 7a.

DETAILED DESCRIPTION

An overview method of one embodiment is presented which introduces the primary components of one embodiment. A detailed discussion of these components then follows. Finally, a method of using the components is discussed in detail.

Figure 1:
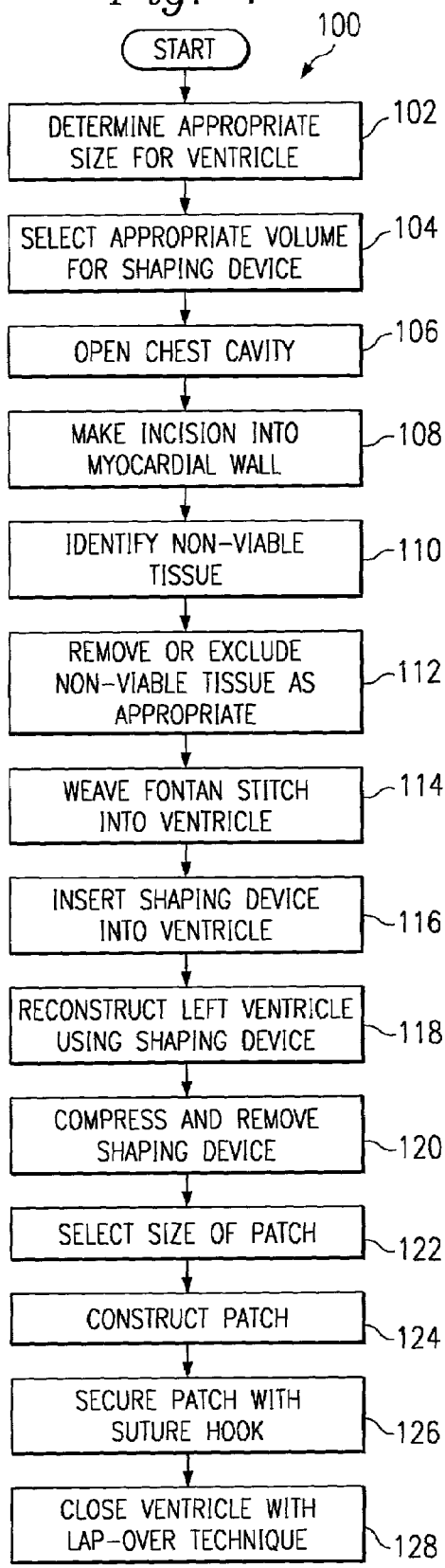
FIG. 1 illustrates one embodiment of a process utilizing several aspects of the present invention.

Overview:

Turning to FIG. 1, there is presented an overview method 100 for performing and using one embodiment of the present invention. A more complete discussion of this method will be presented below. The method 100 may use the following components: a shaping device 200 (FIG. 2a), a patch 300 (FIG. 3a), a sizer 402a (FIG. 4a), and a suture hook 520 (FIG. 5b). Referring back to FIG. 1, at step 102, a surgeon determines the appropriate size for the patient's left ventricle based on the patient's height, weight, body surface area and other patient specific conditions. Once the patient's appropriate ventricle size has been determined, at step 104, the surgeon can then select the appropriate volume for the shaping device 200. At step 106, the surgeon opens up the chest cavity in a conventional manner. An incision is cut into the myocardial wall of an enlarged heart in step 108. At step 110, non-viable tissue is identified. At step 112, the surgeon may remove all or some of the non-viable tissue (i.e., the dyskentic and akinetic areas) of the myocardium. A continuous round stitch, known in the art as a Fontan stitch, may then be woven into the ventricle, at step 114. The stitch produces an annular protrusion, which forms an opening. At step 116, the shaping device 200 may be inserted into the ventricle through this opening. The musculature of the myocardium may be pulled over the shaping device to form a left ventricle having a predetermined volume, shape and contour. The shaping device 200 may then be compressed and removed at step 120. At step 122, with the aid of the sizer 402a, the surgeon may determine the preferred location of and size of the patch 300 which may be placed in the left ventricle. The patch 300 is then cut to size in step 124 and secured to the inside of the myocardium in step 126. At step 128, with the patch 300 suitably placed, the ventricle is closed by joining the myocardial walls over the patch.

Figure 2A:
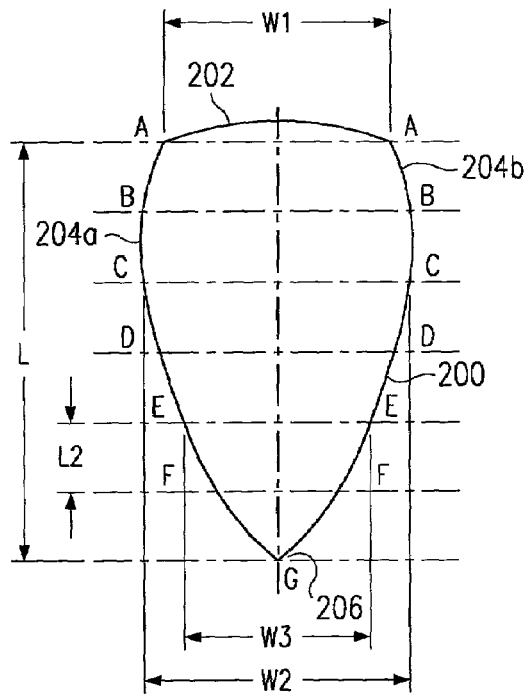
FIG. 2a is a side view of one embodiment of a shaping device.

Description of Components:

The Shaping Device:

FIG. 2a illustrates one embodiment of a shaping device 200. In an inflated condition, the shaping device 200 is pre-shaped to generally model the appropriate volume and shape of the left ventricle.

The shape of the normal heart is of particular interest as it dramatically affects the way that the blood is pumped. The left ventricle which is the primary pumping chamber, is somewhat conical or apical in shape in that it is longer (long axis longest portion from aortic valve to apex) than it is wide (short axis widest portion from ventricle wall to septum) and descends from a base with a decreasing cross-sectional circumference to a point or apex. The left ventricle is further defined by a lateral and posterior ventricle wall and a septum, which extends between the auricles and the ventricles. The pumping of the blood from the left ventricle is accomplished by two types of motion. One of these motions is a simple squeezing motion, which occurs between the lateral wall and the septum. The squeezing motion occurs as a result of a thickening of the muscle fibers in the myocardium. This compresses the blood in the ventricle chamber and ejects it into the body. The thickness changes as the ventricle contracts. This is seen easily by echocardiogram and can be routinely measured.

The other type of motion is a twisting or writhing motion, which begins at the apex and rises toward the base. The rising writhing motion occurs because the heart muscle fibers run in a circular or spiral direction around the heart. When these fibers constrict, they cause the heart to twist initially at the small area of the apex, but progressively and ultimately to the wide area of the base. These squeezing and twisting motions are equally important, as they are each responsible for moving approximately one-half of the blood pumped. Turning now to FIG. 2a, there is shown a shaping device 200 that allows the left ventricle to be reconstructed back to a pre-enlarged operating condition. When the surgeon uses shaping device 200 as a guide in reconstructing the left ventricle, the reconstructed heart can be formed closer to the size and shape of the pre-enlarged heart. Consequently, the heart performs better post operatively than with conventional methods. As illustrated, the shaping device 200 is generally conical or "tear drop" in shape. The length "L" of the shaping device 200 may vary with each patient and will typically be a function of the volume selected for the shaping device. Depending on the patient, the length "L" may be in the three to four inch range to generally match the length of the pre-enlarged left ventricle. A surgeon may select the appropriate volume for the shaping device by estimating the volume of the pre-enlarged left ventricle. The appropriate volume of the pre-enlarged left ventricle for a patient may be estimated to be 50 to 70 cc per square meter of body surface area. The body surface area may be estimated according to the following formula; as known in the art:

$$BSA=0.001*71.84w^{0.428}*h^{0.725}$$

Where:
BSA=body surface area,
w=body weight in kilograms, and
h=body height in centimeters.

The shaping device may be of an "appropriate shape" for a patient. In other words, the shaping device may be of a shape similar to the shape of the left ventricle. In one embodiment, the shaping device 200 may be a generally conical shaped object composed of portions of spherical elements having different radii. Referring back to FIG. 2a, the illustrative embodiment of the shaping device may be divided lengthwise into six sections where each section is a length "L2" apart. L2, therefore, may be determined from the formula: L2=0.1665*L. At line "A—A", a width W1 of the shaping device 200 is approximately 0.543*L. The back surface 202 of the shaping device 200 is generally shaped as a portion of a sphere, having a radius of 0.802*L. At a line "C—C", a width W2 of the shaping device 200 is approximately 0.628*L. The side surfaces 204a and 204b are combinations of portions of spheres with different radii. Between the line A—A and the line C—C, the side surfaces 204a and 204b have a radius of 0.515L.

At a line "E—E", a width W3 of the shaping device 200 is 0.435*L. Between the line C—C and the line E—E, the side surfaces 204a and 204b have a radius of 0.945L. The shaping device 200 narrows from the line designated "E—E" through a line designated as "F—F" to a vertex 206 at point "G". It is important to note that the above discussion is illustrative of only one embodiment of the present invention and is not meant to limit the invention to the above ratios or shapes.

Figure 2B:
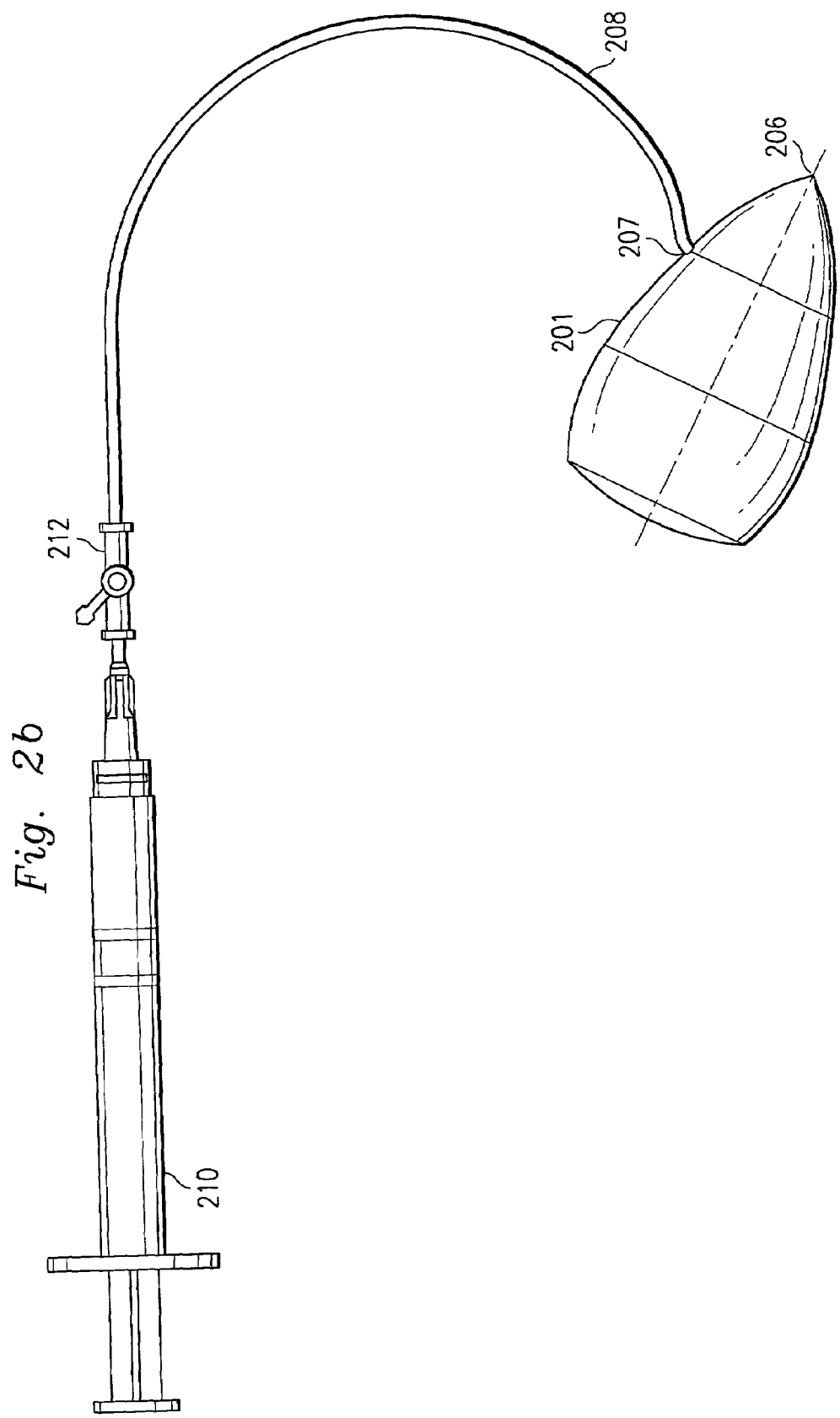
FIG. 2b is a side view of a balloon embodiment of a shaping device.

In some embodiments, such as illustrated in FIG. 2b, the shaping device may be an inflatable balloon 201, having a thickness of in the range of 0.02 to 0.08 inches, preferably 0.03 inches. A distal end of a filler tube 208 may be coupled to a point 207 along the exterior surface of balloon 201. For instance, the point 207 could be located approximately ⅓ along balloon's 201 length, as illustrated in FIG. 2b. In other embodiments, the filler tube 208 may be coupled to vertex 206. Such tubes are well known in the art, and illustratively may be made of materials such as PVC. A proximal end of the filler tube 208 may be connected to a fluid reservoir, such as a syringe 210 which may inject a prespecified amount of fluid into the balloon 201 through the filler tube 208. Also coupled to the distal end of the filler tube 208 may be a fluid control device such a stopcock 212. The injection of fluid through the filler tube 208 inflates the balloon 201 to an inflated condition, as illustrated in FIG. 2b. Once inflated, the fluid inside the shaping device may be prevented from escaping by locking the stopcock 212. This allows the balloon 201 to stay inflated with the proper volume, shape and contour during the reconstruction procedure. The fluid pressure inside the balloon 201 may also be monitored by a pressure transducer, such as a piezoelectric transducer (not shown) coupled to the filler tube 208 with a y-connection (not shown). In other words, one lead of the y-connection would be coupled to a pressure monitor, the other lead would be coupled to the fluid source. Alternatively, the pressure monitor could be coupled to a three way stopcock (not shown), which would monitor the pressure on the filler tube side of the three way stopcock.

The fluid used to fill the balloon 201 may be any one of a number of fluids, such as saline solution or distilled water. Alternatively, another embodiment could use a sealed balloon containing a silicone gel, such as a liquid methyl silicone resin capable of being vulcanized blended with a dimethyl silicone fluid. Such gels are available from Applied Silicon Inc. (Ventura, Calif.). An embodiment using a sealed balloon would not need an external fluid reservoir, such as syringe 210.

The balloon 201 may be conventionally formed on a mandrel (not shown) having dimensions corresponding to the shape, contour and size of the shaping device. As is known in the art, the mandrel can be made of metal, glass or a hardened gelatin. To form the balloon 201, the mandrel is dipped into a polymer solution, which leaves a thin polymer coating on the mandrel surface. After the polymer has cured, the balloon 201 is removed by peeling the thin coating off the mandrel or by flushing mandrel material out of the shaping device.

Shaping Device—Other Embodiments:

The shaping device of the present invention may be made out of a variety of materials in a number of configurations creating a number of embodiments. For instance if the shaping device is molded from a thermoplastic polymer such as PVC or polyethylene or a similar material, the balloon may be "non-expandable" when inflated. In other words, once the balloon is inflated, the balloon 201 will not significantly expand beyond the original shape. To illustrate, several shaping devices might have volumes ranging from 100 cc to 150 cc at 10 cc increments. If a surgeon predetermines that a patient's pre-enlarged left ventricle was 128 cc., then the surgeon might select a non-expandable balloon having a volume of 130 cc. A surgeon could also request a custom non-expandable balloon with a volume specifically sized for an individual patient.

Figure 2C:
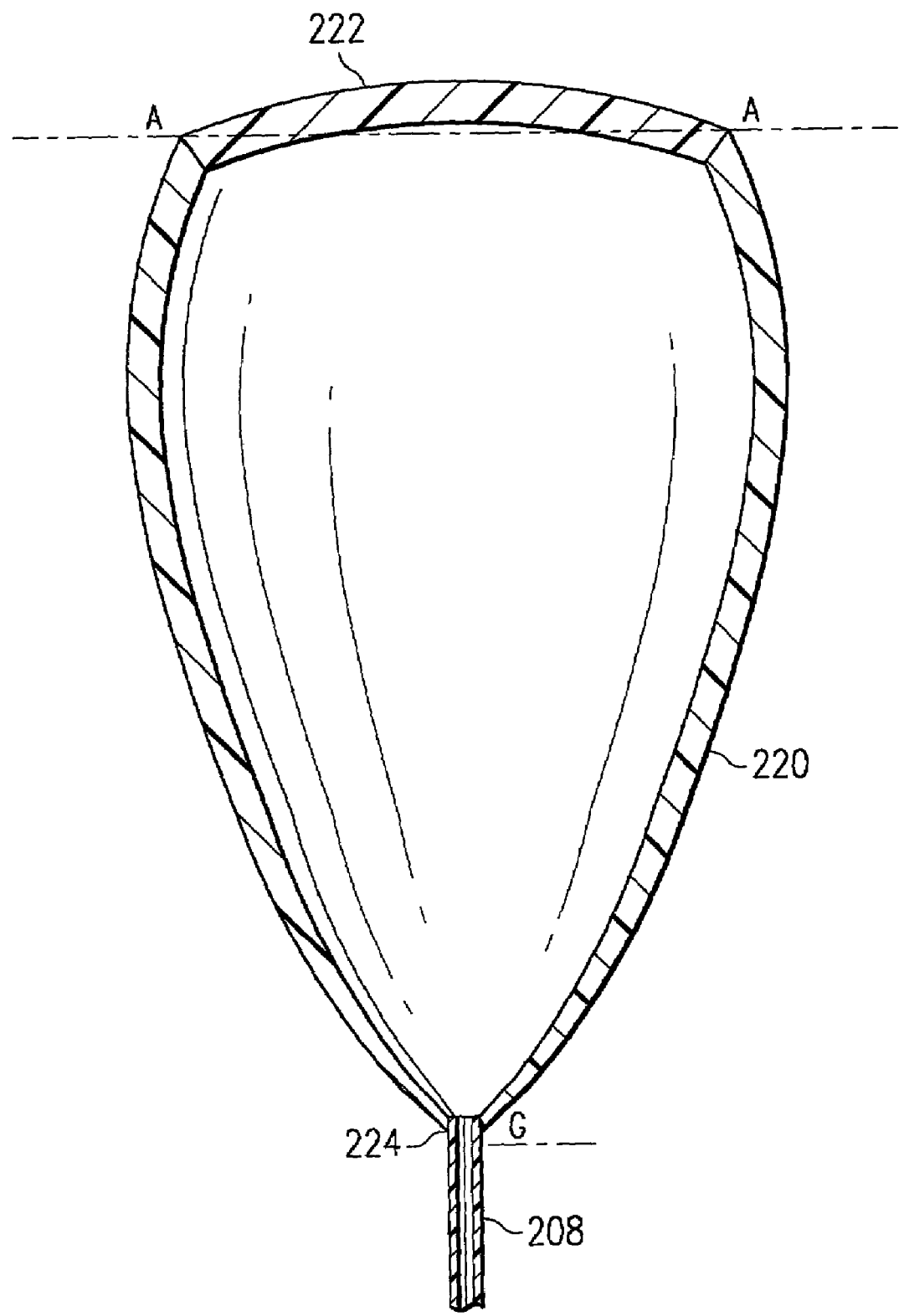
FIG. 2c is a section view of another balloon embodiment of a shaping device.

In contrast, if the balloon 201 is made from an elastomeric material, the balloon 201 may significantly expand. Such elastomeric materials may include latex, polyurethane, silicone, and other elastomers sold under the trade names KRATON (Shell Chemical, New York, N.Y.), C-FLEX (Concept Polymer, Largo, Fla.) and SANTOPRENE (Monsanto, St. Louis, Mo.) Once the balloon is substantially inflated, the influx of additional fluid causes additional expansion of the balloon. Using this embodiment, the surgeon would simply inflate the balloon to a specific volume. The original shape of the balloon may be maintained during this expansion by selectively thickening the walls of the balloon. FIG. 2c is a section view of an embodiment showing thickened walls of an "expandable balloon" 220. An insertion or distal end 222 of the balloon 220 has walls at a maximum thickness. From the line A—A, the wall thickness progressively decreases to a vertex 224 at point G. In some embodiments, the vertex 224 connects to the filler tube 208. The wall thickness will depend on the expansion range of the balloon. For example, for an expansion of 100 to 150 cc, the thickness of the balloon would vary from 0.01" at a thin end to 0.05" at the thick end. Thus, this size or volume of this embodiment may be controlled by controlling the amount and pressure of the fluid injected into the balloon 220.

Figure 2D:
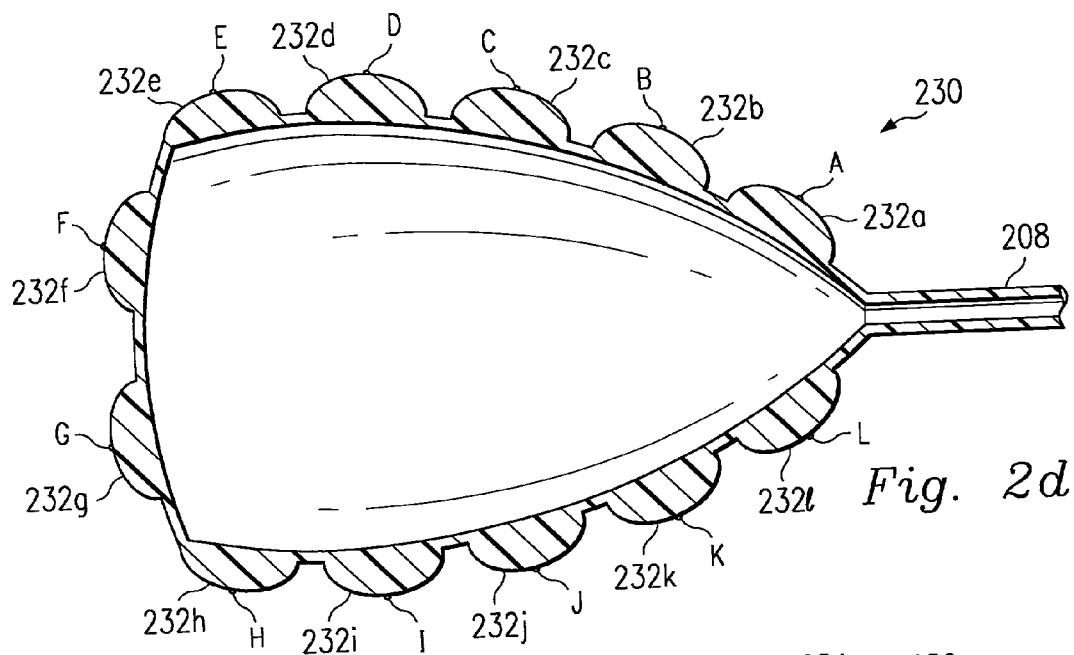
FIG. 2d is a section view of another balloon embodiment of a shaping device.

In another embodiment, the shaping device could have walls that are relatively thick and are coupled to foam spacers or thermoplastic polymer pads surrounding the exterior of the balloon. Turning now to FIG. 2d, there is shown a section view of an embodiment having polymer pads 232a through 232l coupled to the exterior of a balloon 230. In a substantially inflated condition, polymer pads 232a–232l provide a plurality of contact points: "A" through "L". Contact points "A" though "L", if connected, would define a space of approximately the same volume occupied by the balloon 201 (FIG. 2a). Consequently, the balloon 230 would need less fluid for inflation and the polymer pads 232a through 232l would also provide puncture resistance.

Figure 2E:
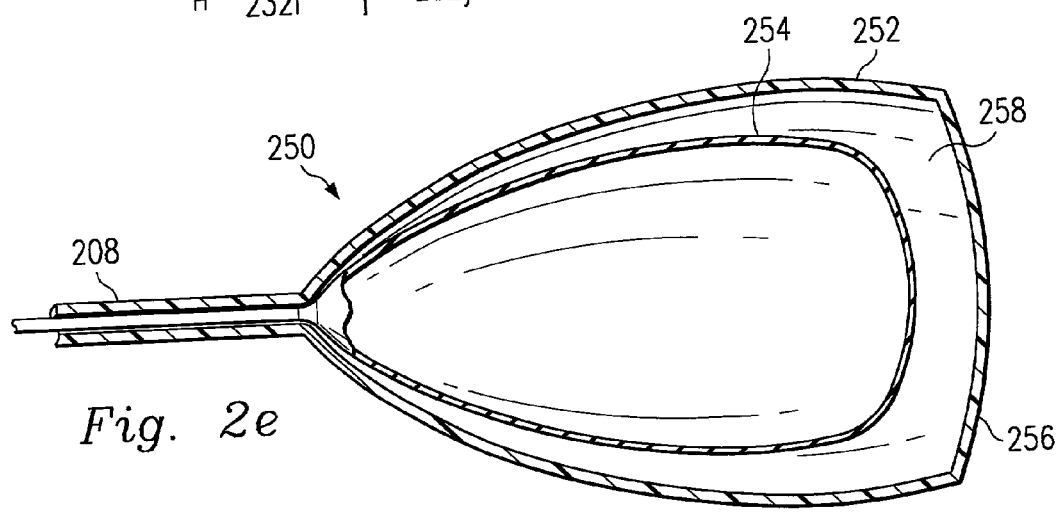
FIG. 2e is a section view of another balloon embodiment of a shaping device.

In yet another embodiment, the shaping device could be a balloon within a balloon. FIG. 2e. illustrates such an embodiment. A balloon 250 is generally shown in FIG. 2e. The balloon 250 comprises a outer balloon 252 and an inner balloon 254. In one embodiment, the inner balloon 254 is inflatable with a fluid, such as saline solution fluid. As in other embodiments, the inner balloon 254 may be inflated through the filler tube 208. A space 256 between the inner balloon 254 and the outer balloon 252 may be pre-filled with a gel 258, such as a silicone gel or saline solution.

Figure 2F:
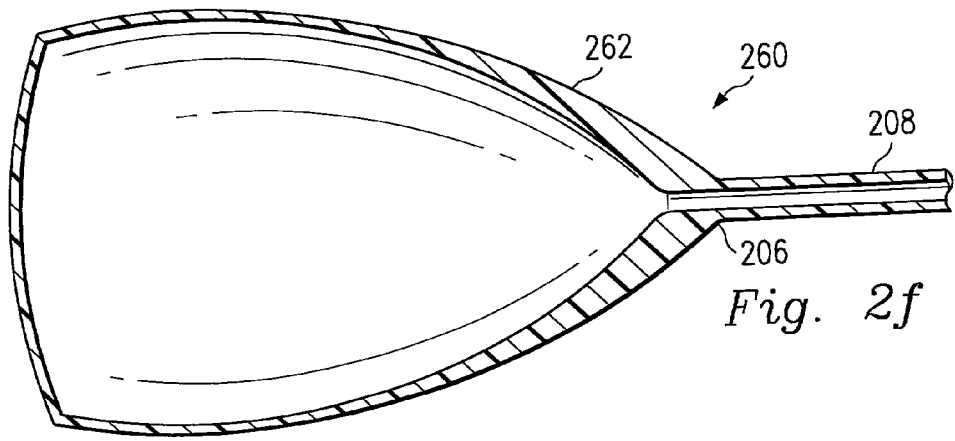
FIG. 2f is a section view of another balloon embodiment of a shaping device.

FIG. 2f is a section view illustrating another embodiment of a balloon 260 formed to be puncture resistant. In this embodiment, the wall 262 proximal to the vertex 206 is progressively thickened to protect the proximal side of the balloon 260 from punctures during the reconstruction procedure. In an alternative embodiment, the wall 262 could be coupled to protective pads located around the vertex 206 to protect the balloon 260 from punctures. In yet another embodiment, the balloon could be made from a thick, self sealing latex rubber. Such latex compounds are well known in the industry.

The shaping device is not limited to polymeric balloon embodiments. FIG. 2g illustrates a shaping device 280 made from a wire skeleton or frame. The wire frame could be made from surgical grade stainless steel, titanium, tantalum, or nitinol, which is a commercially available nickel-titanium alloy material that has shape memory and is superelastic. Nitinol medical products are available from AMF of Reuilly, France, and Flexmedics Corp., of White Bear Lake, Minn.

The shaping device 280 illustrated in FIG. 2g is in an expanded condition. Running through the center of shaping device 280 is a main shaft 282. The main shaft 282 has a distal end 284 and a proximal end 286. At the distal end 284 is a joint 288. Coupled to the joint 288 is a series of back ribs 290a though 290h (only back ribs 290a through 290e are visible in FIG. 2g). Back ribs 290a through 290h are connected to front ribs 292a–292h by hinges 294a though 294h (only front ribs 292a–292e and hinges 294a–294e are visible in FIG. 2g). The proximal end of front ribs 292a through 292e are connected to a collar 296 through a series of hinges (not shown) radially spaced around collar 296. The use of hinges around collar 296 encourages front ribs 292a–292h to form a convex angle with respect to shaft 282 at collar 296.

FIG. 2h shows the shaping device 280 in a collapsed position. In a collapsed position, back ribs 290a–290h and front ribs 292a–292h surround shaft 282 as illustrated in FIG. 2j. FIG. 2j is a section view cut transversely through shaft 282 and the front ribs 292a–292h. In operation, once the shaping device 280 is inserted into the left ventricle, a surgeon may slide collar 296 along shaft 282 towards distal end 284. The force exerted on collar 296 will cause the ribs to buckle radially outward as illustrated in FIG. 2g. Eventually, the front ribs 292a–292h will bend under the applied force. Because the front ribs 292a–292h are under stress, they will tend to push the collar 296 towards proximal end 286. A lock 294 prevents movement towards proximal end 286. Thus, the collar 296 is held firmly in place along shaft 282 by the front ribs 292a–292h exerting a force through collar 296 to lock 294. The lock 294 is spring (not shown) activated and is designed such that the collar 296 may easily slide over the lock when moving from the proximal end 286 to the distal end 288. When the surgeon is ready to remove the shaping device 280, the surgeon may collapse the shaping device 280 by pressing down on lock 294 which will allow the collar 296 to slide past the lock 294 towards the proximal end 286.

Patch

Figure 3A:
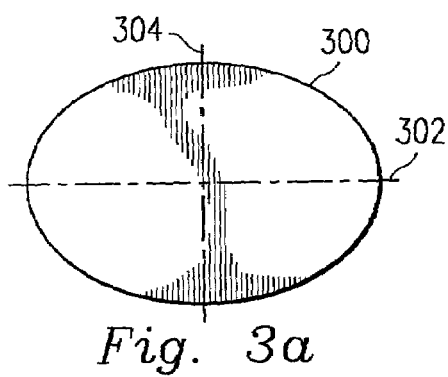
FIG. 3a is a top view of one embodiment of a patch.

As will be explained in greater detail below, a patch is often used in the ventricle reconstruction procedure. A patch is made from sheet material and may be a variety of shapes, including circular, elliptical, or triangular, preferably sized and configured with a shape similar to a Fontan neck, as discussed below. As illustrated in FIG. 3a, an elliptical patch 300 may have a length between 30 and 50 millimeters along a major axis 302 and a width along a minor axis 304 of between 20 and 30 millimeters. The preferable thickness of the patch is in the range of 0.3 to 0.7 mm. The water permeability is preferably less than 5 ml per cm sq. per minute at 120 mm Hg. The burst strength of the patch is preferably 30 to 35 kg/cm. Finally, the 45° angle suture retention strength of the patch should be greater than 3 kg.

The sheet material for the patch 300 may be formed from a biocompatible synthetic material, for example, from polyester, Dacron (Hemoshield) manufactured by the DuPont Corporation, or polytetrafluoroethylene (Gortex). The sheet material may also be autologous pericardium, or some other fixed mammalium tissue such as bovine pericardium or porcine tissue. The biocompatible synthetic material patch may be collagen impregnated to assist in hemostasis, or it may be sprayed with a hemostatic sealant to achieve better and instantaneous hemostasis.

The patch may have markings that enable the movement and position of the patch to be post-operatively observed and analyzed under imaging systems, such as Magnetic Resonance Imaging ("MRI"), x-ray machines, fluoroscopy or other external visualization methods, for post-operative clinical evaluation. Such markings will allow identification of the patch and allow for analysis of the heart's contractility in future post-operative evaluations.

The markings may be radiopaque. Radiopaque markings are made from material that are impenetrable to radiation such as x-rays. Radiopaque markings may be applied to the patch material in a wide variety of methods. For instance, if the patch material is from a woven fabric, then radiopaque threads could be woven into the fabric at regular intervals. Such radiopaque threads could be metal and made from alloys of gold, nitinol, platinum, or stainless steel. Radiopaque threads could also be made of a biocomptabile polymeric material mixed with a metal powder, such as barium sulfate. Radiopaque markings could also be imprinted onto the fabric with radiopaque ink. Such ink is available from Creative Imprints Inc., (Norton, Mass.).

Other techniques for marking the patch 300 might include chemical vapor deposition, physical vapor deposition, electroplating and ion-beam assisted deposition. In ion-beam assisted deposition, an electron beam evaporator is used to create a vapor of atoms that coats the surface of the material.

Radiopaque threads might interfere with MRI scans because MRI is extremely sensitive to metal and metal can substantially mask MRI signals. However, if metal markings are made sufficiently small, they will show as bands in an MRI scan. Using metal fibers 0.1 mm to 0.05 mm to create the grid or pattern by weaving into the patch by ion deposition which could deposit a layer of metal 0.01 mm thick onto the patch material. Small tubular strands filled with fatty acids could also be used as MRI sensitive markings. Such strands could be woven into the patch material.

The markings may be Positron Emission Tomography ("PET") sensitive by making the markings slightly radioactive. However, such markings would probably only be useful for a relatively short time frame after the procedure because of radioactive decay.

The markings may also be attached to the material by a variety of mechanical means such as sewing or weaving the markings into patch material or using microclips. Similarly, the markings such as metal threads may also be attached to the material by adhesive means, such as a bio-compatible glue. Such bio-compatible glues are available from Bioglue, Cryolife Inc. (Kennesaw, Ga.) or Cyanoacrylate, by Loc Tite Corp.

Figure 3B:
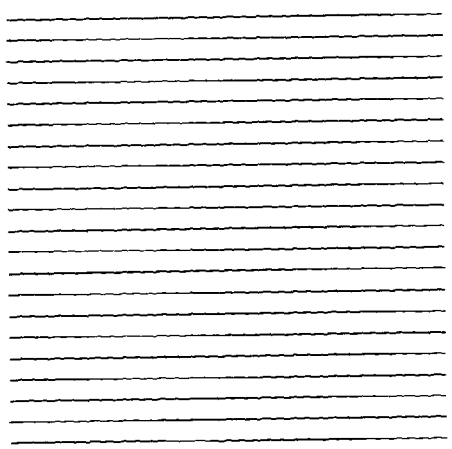
Figure 3C:
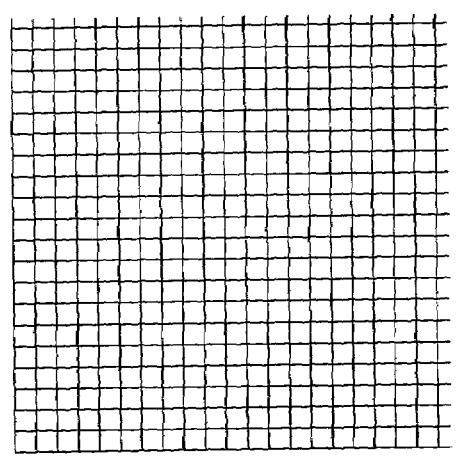
Figure 3D:
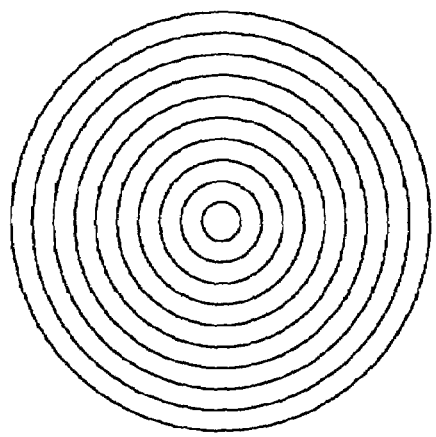
Figure 3E:
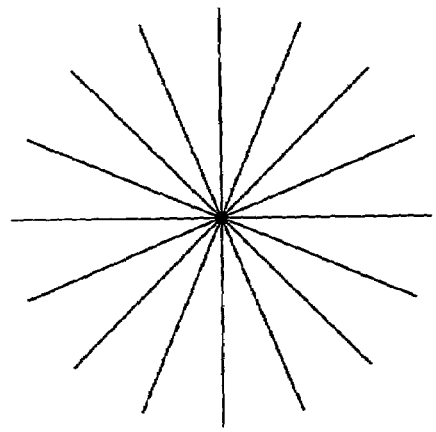

In order to be useful, the markings must be arranged in a pattern that allows post operative evaluation. One such pattern is a series of equally spaced substantially parallel lines as illustrated in FIG. 3b. Another pattern is a grid of substantially parallel lines as illustrated in FIG. 3c. The distance between these parallel lines may be in standard units, such as 1 centimeter. Another pattern could be in the form of concentric circles, as illustrated in FIG. 3d. Yet, another pattern could be a series of lines radiating from a single point at, for instance, a set angle apart. Such a pattern is illustrated in FIG. 3e.

Sizers

Turning now to FIG. 4a, there is illustrated a set of sizers 402a–402d. The sizers 402a–402d are shaped to be the approximate size of the patch 300 (FIG. 3a). Similar to the patch, the sizers 402a–402d will be of various geometries, length and width combinations. For illustrative purposes, the sizers 402a–402d discussed herein will be elliptical in shape. For posterior repairs to the ventricle, however, the sizers may have a general triangular shape. Referring back to FIG. 4a, the length of the sizers along a major axis 403 may be in the range of 2 to 7 cm in length. The length along a minor axis 405 may be 1 to 5 cm in length. The sizers may have a connection 406 for attachment to a handle 404 (FIG. 4b). The sizers 402a–402d can be made out of plastic or stainless steel or any rigid material. Four sizers 402a–402d are illustrated in FIG. 4a, however, any number of sizers in a variety of shapes could be provided.

Turning now to FIG. 4b, the handle 404 may also be made from stainless steel, plastic or any other suitable material. The handle 404 includes a shaft 408 having a proximal end 410 and a distal end 412. The distal end 412 couples to the connection 406 of the sizers 402a–402d. The proximal end 410 is coupled to a hand grip 414. The hand grip 414 is sized to fit a human hand. Such hand grips are well known in the art. A surgeon may connect any of the sizers 402a–402d to the handle 404. The use of handle 404 with a sizer allows the surgeon to easily estimate the size of the opening to be patched by holding the sizer up to and into the opening. If the sizer is to small, another one may be selected. This process may be repeated until the surgeon feels he has a sizer of the correct shape and size. As will be explained in greater detail below, once the proper size has been determined the sizer may be placed on material and be used as a template to cut the patch 300 to the appropriate size.

FIG. 4c is a section view illustrating the connection 406 between the distal end 412 of shaft 408 and the sizer 402a. In this embodiment, the connection 406 comprises a circular opening 422. Embedded in the walls of the opening 422 and running through the opening 422 is a rod 420. The rod 420 may be made of surgical stainless steel or another appropriate rigid material. In the illustrative embodiment, the distal end 412 includes a slot 425 with angular walls forming two flanges 423a and 423b. At the base of the slot 425 is a circular groove. The circular grove runs generally parallel to the slot 425 and has an interior diameter slightly larger than the exterior diameter of rod 420. The base of the slot 425 is slightly smaller than the diameter of rod 420. When distal end 412 is inserted into circular groove, flanges 423a and 423b slide over rod 420 until rod 420 is in the circular groove. Thus, flanges 423a and 423b are "snapped" over rod 420, and thus, will keep rod 420 in the cylindrical groove. The sizer 402a may rotate with respect to shaft 408. The sizer 402a may be removed from handle 404 by pulling on the sizer 402a which causes a sufficient amount of force on rod 420 to lift flanges 423a and 423b over rod 420. In other embodiments, connection 406 may be a screw connection.

In another embodiment, the sizers may have a cutting edge which can be used to cut the patch 300 to the appropriate shape. Turning now to FIG. 4d, a sizer 430 is shown connected to the handle 408. In this embodiment, the sizer 430 may have a ridge 432 concentric to the shape of the sizer 430. The ridge 432 allows a surgeon to accurately estimate the size of the opening by placing the ridge 432 into the opening. The sizer 430 may also have a circumferential flange or lip 434 around the perimeter of the sizer to assist in defining the patch size. The patch will typically be slightly larger than the size of the opening. The width of the lip 434 will preferably have a constant width around its circumference, typically in the range between 5 and 8 centimeters. A cutting edge 434' may also be coupled to the perimeter of the lip. In operation, the surgeon may use the sizer as illustrated in FIG. 4d to estimate the size of the opening, remove the sizer 430 from the handle 408, turn the sizer 430 over with respect to the handle 408, and re-attach the sizer 430 to the handle 408. The cutting edge 434' may then be used to cut the patch material to the correct size and shape by pressing the cutting edge into the patch material.

A set of cutting dies could also be provided which corresponds to the set of sizers. In other words, for each sizer provided in a set of sizers, there would be a corresponding cutting die, sized to be slightly larger than the sizer. Once a surgeon has determined the correct sizer, he could then select the corresponding cutting die and use the cutting die to cut the patch material to the appropriate size. Alternatively, a set of pre-cut patches could be provided, each pre-cut patch corresponding to a particular sizer in the set of sizers. The use of pre-cut patches would eliminate the need to cut the patch material to the required shape. The pre-cut patches may also have pre-printed suture lines which may be used as a guide for the surgeon when attaching the patch to the heart.

FIG. 4e illustrates an embodiment of a sizer 440 having a protrusion 442 concentric to the shape of the sizer 440. The protrusion 442 may also be used to define a suture line on the patch material by pressing the protrusion 442 against the patch material causing an indentation in the patch material which the surgeon can use as a guide to suture the patch. Turning now to FIG. 4f, which illustrates embodiment of a sizer 450 having a slot or groove 452 concentric to the shape of the sizer. The groove 452 may be used by the surgeon to define a suture line by allowing the surgeon to use a marking instrument, such as a pen, to trace the suture line on the patch material.

FIG. 4g illustrates yet another embodiment of a sizer. The sizer 460 may be a malleable wire 462 coupled to movable legs 464a–464d (464a and 464b are visible in FIG. 4g). The moveable legs 464a–464d are coupled to a handle 466. The handle 466 includes a shaft 468 having a proximal end 470 and a distal end 472. The distal end 472 couples to the movable legs 464a–464d. The proximal end 470 is coupled to a hand grip 474. The hand grip 474 is similar to the handgrip 414 of FIG. 4b. FIG. 4h is a section view of the sizer 460 cut through the movable legs 464a–464d. The malleable wire 462 may be manipulated by the surgeon into any appropriate shape. Additionally, because one end 466 of the malleable wire 462 is free to slide past the moveable legs 464a and 464d, the perimeter of the shape formed by the wire may be lengthened or shortened as desired.

Patch Holder

Turning now to FIG. 5a, there is illustrated a patch holder 500. The patch holder 500 comprises a patch plate 502 coupled to legs 504a–504d (504a and 504b are visible in FIG. 5a). The legs 504a–504d are coupled to a handle 506, which is similar to handle 466 discussed above. The patch plate 502 has an adhesive means on side 508, such as an adhesive backing or nylon hooks, which temporarily adheres to the patch. In operation, after a surgeon has constructed the appropriate patch, the surgeon may use patch holder 500 to place the patch into the opening, after suturing has begun, the patch holder may be removed, leaving the patch in place.

Suture Hook

Turning now to FIG. 5b, there is illustrated a suture hook 520. The suture hook 520 is "L" shaped and made of stainless steel, plastic or another rigid material. The suture hook 520 has a long leg 522 which may be approximately 6 inches long. Coupled to long leg 522, is short leg 524 which may be in the range of one-eighth to one-quarter inch long. The suture hook 520 is adapted to be used to pull up on the sutures in the patch 300 to secure the patch 300 to the heart.

Kit

Figure 6:
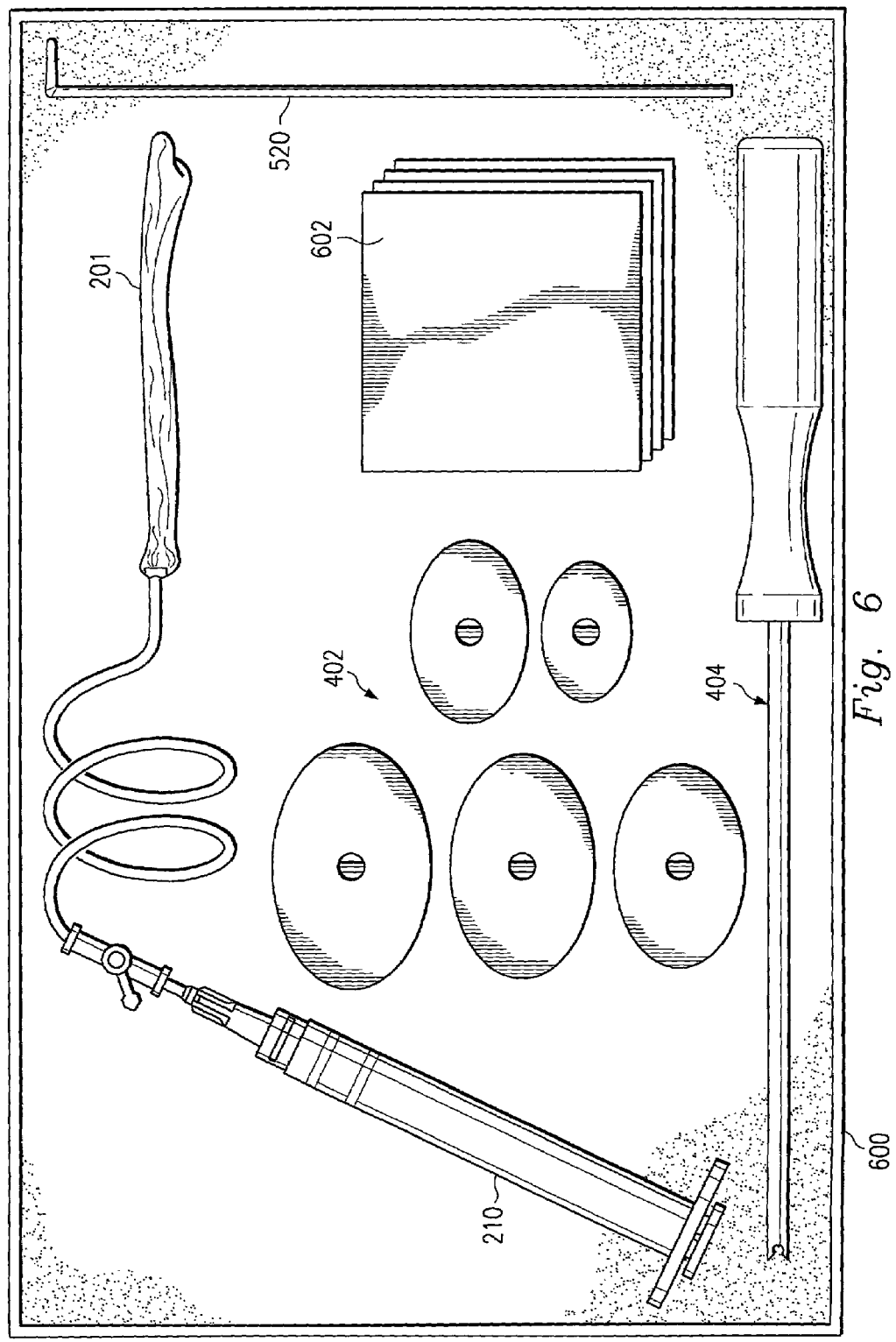
FIG. 6 is a top view of one embodiment of a kit for surgically reshaping a ventricle.

In yet another embodiment of the present invention, a kit 600 for surgically reshaping the left ventricle of the heart is illustrated in FIG. 6. The kit 600 may include any of the components discussed above, including: the balloon 201 coupled to the syringe 210, a set of the sizers 402 in various shapes and sizes, a handle 404 to attach to the sizers 402, material 602 for creating the patch 300 (not shown), the suture hook 520 and, the patch holder 500 (not shown). The components of the kit 600 may be packaged in a sterile manner as known in the relevant art.

Operation

With the primary purpose of restoring the ventricle's size, shape and contour, the intent of the procedure initially is to remove that portion of the wall, which is not capable of contracting. Such portions include the scarred dyskinetic segments, which are easy to see visually, and may also include akinetic segments, which do not contract.

Figure 7A:
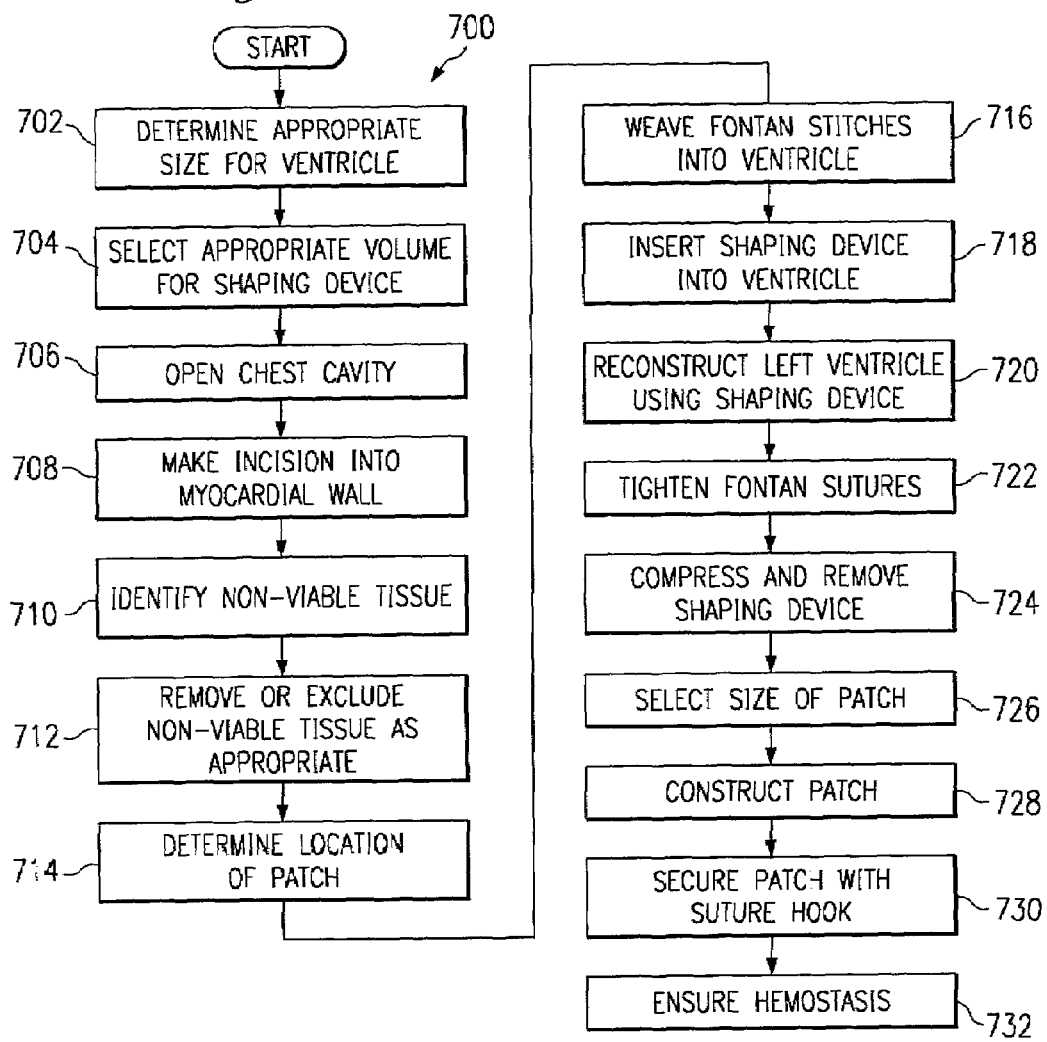
FIG. 7a illustrates one embodiment of a process utilizing several aspects of the present invention.
Figure 7B:
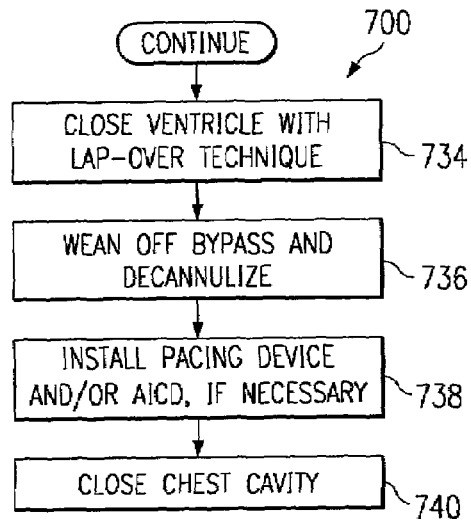

Referring now to FIG. 7, which illustrates generally a method 700 for performing and using at least one embodiment of the present invention. At step 702, a surgeon determines the appropriate size for the patient's left ventricle based on the patient's height, weight, body surface area and other patient specific conditions (as discussed previously in reference to FIG. 2a). Once the patient's appropriate ventricle size has been determined, at step 704, the surgeon can then select the appropriate volume for the shaping device.

In step 706, the patient's chest cavity is opened up in a conventional manner. In step 708, an incision is cut into the myocardial wall of the dilated heart. If the surrounding tissue is dyskinetic, it will typically be formed entirely of thin, elastic scar tissue. It is the elasticity of this scar tissue, which causes the detrimental ballooning, or bulging effects previously discussed.

In step 710, a determination as to where the akinetic portions of the tissue begin and end must be made. The determination between viable and non viable tissue can be made by multiple methods, including: visual inspection, electrical methods, marking with dyes, echocardiography, radionuclear imaging, and palpation of a beating heart.

The electrical methods might include the use of an electromyogram which detects electrical impulses from active tissue to distinguish between the akinetic and viable tissue. Positron Emission Tomography (PET) scanning, Single Proton Emissions Computer Tomography and Electrical Mapping Electrophysiology are all other examples of a method to determine viable tissue from akinetic tissue with by electrical means. With Electrical Mapping Electrophysiology, a catheter is inserted into the heart to find areas void of electrical activity.

Marking with dyes can be accomplished by staining the myocardium tissue with a dye that adheres to viable tissue and does not adhere to scar tissue. Triphenyltetrazolium chloride, Tropinin I or T, and Creatine Kinase are all examples of dyes that perform this marking function.

Once the extent of the non-viable areas are determined, in step 712, the portion of the tissue in the ventricle and septal walls may be excised from the epicardium from the incision to the borderline separating akinetic tissue from viable tissue. This border between akinetic and viable tissue becomes the preferred location of the patch and forms an imaginary circumferential line between the non viable areas and viable areas of the myocardium.

In step 714, the preferred location of the patch 300 is determined relative to the circumferential line. In step 716, a continuous Fontan stitch may be placed in proximity to the line, along the long axis of the heart. The Fontan stitch produces an annular protrusion, which forms a neck relative to the circumferential line. The annular protrusion may be further defined by placing a rim support around its perimeter. This neck initially may have a round circular configuration. A second Fontan stitch may be placed 90 degrees from the initial stitch along the short axis of the heart. Other stitches may be placed as needed to form the heart to the shaping device. The stitch will serve to shape the heart along the short axis of the heart if needed.

In step 718, the shaping device 200 may then be inserted into the ventricle. The shaping device 200 is then inflated or expanded, the volume of which is equivalent to the appropriate volume of the ventricle for the patient. The shaping device 200 provides the model upon which the ventricle can be shaped and contoured through the use of the Fontan suture in step 720. The Fontan suture may then be tightened with the aid of the suture hook 520, in step 722. As the suture or sutures are tightened, the musculature of the myocardium will form the physiologically correct volume, shape and contour over the shaping device. The appropriately ovalshaped opening in the neck defines the area where the patch will be placed. Once the suture is tightened down, the shaping device 200 may be collapsed and removed in step 724.

The size of the opening in the neck formed by the Fontan stitch will vary from patient to patient. If the patch 300 is used to close the ventricle, the surgeon should determine the size of the patch to be used (step 726). To determine the appropriate size of the patch, the surgeon may connect any of the sizers 402a–402d to the handle 404 to measure the size of the opening, and thus, the size patch 300 that is needed to fit into the neck formed by the Fontan stitch or stitches. In step 728, the surgeon may then construct a patch. In embodiments with different sizers, once the proper sizer has been selected, the sizer can be placed on the patch and be used as a template to cut the patch 300 to the appropriate size. Alternatively, a surgeon may select a precut patch.

In a preferred method for placing the patch, continuous or interrupted sutures can be threaded through the rim covered annular protrusion. The rim covering acts as a large continuous pledget along the perimeter. After the patch has been moved into position on the neck, the sutures can be tied, in step 730.

Alternatively, in cases of extensive nonfibrotic trabecular tissue on the lateral ventricle, another suture method can be placement of mattressed braided sutures over a pericardial strip from outside the ventricle to its interior through the inner oval of the patch. This procedure can be done in conjunction with other procedures such as; Mitral valve repair, ablation of ventricular arrhythmias for treatment of refractory ischemic ventricular tachycardia.

With the patch suitably placed, in step 732, the suture line can be sprayed with a hemostatic agent or an agent can be applied to achieve better and instantaneous hemostasis. In step 734, the operative site can be closed by joining or folding over the myocardial walls. Care should be taken not to distort the right ventricle by folding the septum wall over the ventricular wall. Alternatively, the lateral wall can be disposed interiorly of the septum wall so a majority of the force on the patch is diverted to the lateral wall. These walls can be overlapped in close proximity to the patch in order to avoid creating any cavity between the patch and the walls.

When air evacuation is confirmed by transesophageal echo, the patient can be weaned off bypass usually with minimal, if any inotropic support. Decannulisation may be accomplished with conventional methods (step 736).

As is well known, the human heart contains an electrical conduction system which sends electrical impulses to spark the heart muscle into regular cycles of contraction. This conduction system includes a Sinoatrial node (SA node), Atrioventricular Node (AV node), and Purkinie Fibers which act as conduits for the electrical pulses. The SA node is located in the right atrium. The electrical impulse leaves the SA node and travels to the right and left Atria, causing them to contract together. This takes 0.04 seconds. There is now a natural delay to allow the Atria to contract and the Ventricles to fill up with blood. The electrical impulse has now traveled to the Atrioventricular Node (AV node). The electrical impulse now goes to the Bundle of His, then it divides into the Right and Left Bundle Branches where it rapidly spreads using Purkinje Fibers to the muscles of the Right and Left Ventricle, causing them to contract at the same time.

Because ventricular restoration may compromise the conduction system due to the fact that a ventricle portion has been severed or excluded, the pacing or rhythm of the impulses between the right and left ventricles of the heart may get out of synchronization after ventricular restoration. This asynchronous pacing contributes to a reduced output by the left ventricle. Thus, restoring or assuring synchronization would assist the reconstructed left ventricle to maximize the output of the left ventricle. Synchronization may be restored or controlled by implanting a pacemaker or a Biventricular pacing device ("BVP") before closing the chest cavity.

A pacemaker comprises: (1) an implantable controller that sets the heart rate to the desired interval, and (2) two leads that deliver electrical impulses to specific regions of the heart (i.e., one lead is placed in the right atrium and the second lead in right ventricle) to artificially cause contractions of the ventricle at the appropriate time and synchronization. In contrast, BVPs have a third lead designed to conduct signals directly into the left ventricle. When using a BVP, one lead is placed in the right atrium, the second lead in right ventricle and third lead is placed to pace the left ventricle (i.e., in a tributary of the coronary sinus in the left ventricle). Thus, with a BVP, simultaneous electrical impulses are given to both left and right ventricles so the time delay in traveling of electrical impulse is significantly reduced which aids in restoring the normal physiology of the heart and improves the pumping action of the heart.

Pacemakers and biventricular pacing devices are available from Medtronic, Inc. (Minneapolis, Minn.), Guidant Corporation (Menlo Park, Calif.), and St. Jude Medical Inc. (St. Paul, Minn.).

The mortality associated with ventricular restoration is primarily from sudden death caused from extremely fast arrthymias. The higher risk of arrthymias may be caused from the removal of a portion of the left ventricle. This risk may be prevented by implanting a defibrillator at the time of the ventricle restoration. The automatic implantable cardioverter/defibrillator is commonly referred to as an AICD. The AICD is a device that is similar to a pacemaker, but continuously monitors the heart rhythm. If the AICD detects an abnormally fast or slow heart rhythm, it either electrically paces the heart very fast or delivers a small electrical shock to the heart to convert the heart rhythm back to normal.

Some BVP devices have defibrillators built into the circuitry that controls the pacing. Implanting a bi-ventricular pacing device with defibrillator after surgical ventricular restoration will not only optimize the output of the ventricle but also prevent many sudden deaths.

After a BVP has been installed in step 738, closure of the chest cavity may be accomplished in step 740 by conventional methods.

It is further understood that other modifications, changes and substitutions are intended in the foregoing disclosure and in some instances some features of the disclosure will be employed without corresponding use of other features. Accordingly, it is appropriate that the appended claims be construed broadly and in a manner consistent with the scope of the disclosure.

What is claimed is:

1. A method for reconstructing an enlarged left ventricle of a human heart, comprising:
   opening the enlarged left ventricle;
   placing a shaper into the enlarged left ventricle, the shaper having a size and shape substantially equal to the size and shape of an appropriate left ventricle;
   reforming the enlarged left ventricle over the shaper;
   removing the shaper from the enlarged left ventricle; and
   suturing a patch to an interior of the left ventricle closing the opening, such that the enlarged left ventricle is reconstructed into a shape and volume of an appropriate left ventricle.

2. The method of claim 1, wherein the reforming step further comprises:
   pulling the enlarged left ventricle over the shaper;
   suturing the left ventricle such that an interior surface of the left ventricle substantially conforms to the shape of the shaper; and
   partially closing the opening.

3. The method of claim 1, further comprising excluding scar tissue from the viable tissue.

4. The method of claim 1, further comprising:
   determining a demarkation line between non-viable tissue and viable tissue;
   excluding some of the non-viable tissue;
   placing at least one suture along the demarkation line; and
   pulling the suture such that the left ventricle is pulled around the shaper.

5. The method of claim 4, wherein the determining of the demarkation line further comprises engaging a wall of the left ventricle of a beating heart to sense tactile feedback.

6. The method of claim 4, wherein the determining of the demarkation line further comprises visually determining akinetic and viable tissue.

7. The method of claim 4, wherein the determining of the demarkation line further comprises detecting electrical pulses from the viable tissue.

8. The method of claim 4, wherein the closing step comprises suturing a patch along the at least one demarkation line.

9. A method for reshaping a left ventricle of a human heart, comprising:
   positioning a shaper in the left ventricle;
   reshaping at least a portion of the left ventricle about the shaper such that at least a portion of the left ventricle substantially conforms to a predetermined shape of the shaper; and
   suturing a patch to an interior of the left ventricle.

10. The method of claim 9, further comprising excluding scar tissue from viable tissue.

11. The method of claim 9, wherein at least a portion of the left ventricle substantially corresponds to the predetermined shape of the shaper.

12. The method of claim 9, further comprising:
    determining a demarkation line between non-viable tissue and viable tissue;
    excluding at least some of the non-viable tissue;
    placing at least one suture along at least a portion of the demarkation line; and
    pulling the suture such that the left ventricle is pulled around the shaper.

13. The method of claim 12, wherein the determining of the demarkation line further comprises engaging a wall of the left ventricle of a beating heart to sense tactile feedback.

14. The method of claim 12, wherein the determining of the demarkation line further comprises visually determining akinetic and viable tissue.

15. The method of claim 12, wherein the determining of the demarkation line further comprises detecting electrical pulses from viable tissue.

16. The method of claim 12, further comprising suturing a patch along at least a portion of one of the demarkation lines.

17. The method of claim 9, wherein the shaper has a short axis and a long axis.

18. The method of claim 9, wherein the shaper has a short axis and a long axis, and wherein the ratio of the short axis to the long axis is about 0.3 to about 0.7.

19. The method of claim 9, wherein the shaper is substantially ellipsoid in shape.

20. The method of claim 9, wherein the shaper is substantially conical in shape.

21. The method of claim 9, wherein the shaper is substantially pear shaped.

22. The method of claim 9, wherein the shaper is substantially tear drop shaped.

23. The method of claim 9, wherein the reshaping comprises pressing at least a portion of the left ventricle against the shaper.

24. The method of claim 9, wherein the reshaping comprises using the firmness of the shaper to resist deformation of the shaper when at least a portion of the left ventricle is pressed against the shaper.

25. The method of claim 9, further comprising demarking between non-viable tissue and viable tissue of the left ventricle.

26. The method of claim 9, wherein the reshaping comprises pressing at least a portion of the left ventricle against the shaper and using the firmness of the shaper to resist deformation of the shaper when at least a portion of the left ventricle is pressed against the shaper.

27. The method of claim 9, further comprising demarking between non-viable tissue and viable tissue of the left ventricle, and wherein the reshaping comprises pressing at least a portion of the left ventricle against the shaper and using the firmness of the shaper to resist deformation of the shaper when at least a portion of the left ventricle is pressed against the shaper.

28. The method of claim 9, wherein the reshaping comprises pressing at least a portion of the left ventricle against the shaper and using the firmness of the shaper to resist deformation of the shaper when at least a portion of the left ventricle is pressed against the shaper, and further comprising attaching a patch to at least a portion of the left ventricle.

29. The method of claim 9, further comprising excluding at least some of the non-viable tissue of the left ventricle.

30. The method of claim 9, further comprising:
excluding at least some of the non-viable tissue;
placing at least one suture along at least a portion of the demarkation line; and
pulling the suture such that the left ventricle is pulled around the shaper.

31. The method of claim 30, further comprising attaching a patch along at least a portion of one of the demarkation lines.

32. The method of claim 30, further comprising suturing a patch along at least a portion of one of the demarkation lines.

33. A method for reshaping a left ventricle of a heart, comprising:
positioning a shaper in the left ventricle;
positioning a gel in a hollow of the shaper to expand the shaper to a predetermined shape;
reshaping at least a portion of the left ventricle about the shaper such that at least a portion of the left ventricle substantially conforms to the predetermined shape of the shaper; and
suturing a patch to an interior of the left ventricle.

34. The method of claim 33, further comprising excluding scar tissue from viable tissue.

35. The method of claim 33, wherein at least a portion of the left ventricle substantially corresponds to the predetermined shape of the shaper.

36. The method of claim 33, further comprising:
determining a demarkation line between non-viable tissue and viable tissue;
excluding at least some of the non-viable tissue;
placing at least one suture along at least a portion of the demarkation line; and
pulling the suture such that the left ventricle is pulled around the shaper.

37. The method of claim 36, wherein the determining of the demarkation line further comprises engaging a wall of the left ventricle of a beating heart to sense tactile feedback.

38. The method of claim 36, wherein the determining of the demarkation line further comprises visually determining akinetic and viable tissue.

39. The method of claim 36, wherein the determining of the demarkation line further comprises detecting electrical pulses from viable tissue.

40. The method of claim 36, further comprising suturing a patch along at least a portion of one of the demarkation lines.

41. A method for reshaping a left ventricle of a human heart, comprising:
positioning a shaper in the left ventricle;
expanding an expander positioned in a hollow of the shaper to expand the shaper to a predetermined shape;
reshaping at least a portion of the left ventricle about the shaper such that at least a portion of the left ventricle substantially conforms to the predetermined shape of the shaper; and
excluding scar tissue from viable tissue.

42. The method of claim 41, further comprising suturing a patch to an interior of the left ventricle.

43. The method of claim 41, wherein at least a portion of the left ventricle substantially corresponds to the predetermined shape of the shaper.

44. The method of claim 41, further comprising:
determining a demarkation line between non-viable tissue and viable tissue;
excluding at least some of the non-viable tissue;
placing at least one suture along at least a portion of the demarkation line; and
pulling the suture such that the left ventricle is pulled around the shaper.

45. The method of claim 44, wherein the determining of the demarkation line further comprises engaging a wall of the left ventricle of a beating heart to sense tactile feedback.

46. The method of claim 44, wherein the determining of the demarkation line further comprises visually determining akinetic and viable tissue.

47. The method of claim 44, wherein the determining of the demarkation line further comprises detecting electrical pulses from viable tissue.

48. The method of claim 44, further comprising suturing a patch along at least a portion of one of the demarkation lines.

49. A method for reshaping a left ventricle of a human heart, comprising:
positioning a shaper in the left ventricle;
expanding an expander positioned in a hollow of the shaper to expand the shaper to a predetermined shape;
reshaping at least a portion of the left ventricle about the shaper such that at least a portion of the left ventricle substantially conforms to the predetermined shape of the shaper; and
suturing a patch to an interior of the left ventricle.

50. The method of claim 49, wherein at least a portion of the left ventricle substantially corresponds to the predetermined shape of the shaper.

51. The method of claim 49, further comprising:
determining a demarkation line between non-viable tissue and viable tissue;
excluding at least some of the non-viable tissue;
placing at least one suture along at least a portion of the demarkation line; and
pulling the suture such that the left ventricle is pulled around the shaper.

52. The method of claim 50, wherein the determining of the demarkation line further comprises engaging a wall of the left ventricle of a beating heart to sense tactile feedback.

53. The method of claim 51, wherein the determining of the demarkation line further comprises visually determining akinetic and viable tissue.

54. The method of claim 51, wherein the determining of the demarkation line further comprises detecting electrical pulses from viable tissue.

55. The method of claim 51, further comprising suturing a patch along at least a portion of one of the demarkation lines.

56. A method for reshaping a left ventricle of a human heart, comprising:
positioning a shaper in the left ventricle;
expanding an expander positioned in a hollow of the shaper to expand the shaper to a predetermined shape;
reshaping at least a portion of the left ventricle about the shaper such that at least a portion of the left ventricle substantially conforms to the predetermined shape of the shaper;
determining a demarkation line between non-viable tissue and viable tissue;
excluding at least some of the non-viable tissue;
placing at least one suture along at least a portion of the demarkation line; and
pulling the suture such that the left ventricle is pulled around the shaper.

57. The method of claim 56, wherein at least a portion of the left ventricle substantially corresponds to the predetermined shape of the shaper.

58. The method of claim 56, wherein the determining of the demarkation line further comprises engaging a wall of the left ventricle of a beating heart to sense tactile feedback.

59. The method of claim 56, wherein the determining of the demarkation line further comprises visually determining akinetic and viable tissue.

60. The method of claim 56, wherein the determining of the demarkation line further comprises detecting electrical pulses from viable tissue.

61. The method of claim 56, further comprising suturing a patch along at least a portion of one of the demarkation lines.

62. A method for reshaping a left ventricle of a human heart, comprising:
positioning a shaper in the left ventricle, wherein the left ventricle has a first shape;
using the shaper as a model to reshape at least a portion of the left ventricle such that the reshaped left ventricle has a second shape;
removing the shaper from the left ventricle; and
attaching a patch to an interior of the left ventricle.

63. The method of claim 62, wherein the second shape is substantially similar to the shape of an appropriate left ventricle of a heart.

64. The method of claim 62, wherein the first shape is the shape of an enlarged left ventricle of a heart.

65. The method of claim 62, wherein the first shape is substantially spherical.

66. The method of claim 62, wherein the first shape comprises a greater volume relative to the second shape.

67. The method of claim 62, wherein at least a portion of the second shape substantially corresponds to at least a portion of a size of the shaper.

68. The method of claim 62, wherein at least a portion of the second shape substantially corresponds to at least a portion of a shape of the shaper.

69. The method of claim 62, wherein at least a portion of the second shape substantially corresponds to at least a portion of a size of the shaper, and wherein at least a portion of the second shape substantially corresponds to at least a portion of a shape of the shaper.

70. The method of claim 62, wherein the shaper has a short axis and a long axis.

71. The method of claim 62, wherein the shaper has a short axis and a long axis, and wherein the ratio of the short axis to the long axis is about 0.3 to about 0.7.

72. The method of claim 62, wherein the shaper is substantially ellipsoid in shape.

73. The method of claim 62, wherein the shaper is substantially conical in shape.

74. The method of claim 62, wherein the shaper is substantially pear shaped.

75. The method of claim 62, wherein the shaper is substantially tear drop shaped.

76. The method of claim 62, wherein the reshaping comprises pressing at least a portion of the left ventricle against the shaper.

77. The method of claim 62, wherein the reshaping comprises using the firmness of the shaper to resist deformation of the shaper when at least a portion of the left ventricle is pressed against the shaper.

78. The method of claim 62, further comprising determining a demarkation line between non-viable tissue and viable tissue of the left ventricle.

79. The method of claim 62, further comprising demarking between non-viable tissue and viable tissue of the left ventricle.

80. The method of claim 62, wherein the reshaping comprises pressing at least a portion of the left ventricle against the shaper and using the firmness of the shaper to resist deformation of the shaper when at least a portion of the left ventricle is pressed against the shaper.

81. The method of claim 62, further comprising demarking between non-viable tissue and viable tissue of the left ventricle, and wherein the reshaping comprises pressing at least a portion of the left ventricle against the shaper and using the firmness of the shaper to resist deformation of the shaper when at least a portion of the left ventricle is pressed against the shaper.

82. The method of claim 62, wherein the reshaping comprises pressing at least a portion of the left ventricle against the shaper and using the firmness of the shaper to resist deformation of the shaper when at least a portion of the left ventricle is pressed against the shaper, and further comprising attaching a patch to at least a portion of the left ventricle.

83. The method of claim 62, further comprising:
engaging a wall of the left ventricle of a beating heart to sense tactile feedback; and
determining a demarkation line between non-viable tissue and viable tissue of the left ventricle.

84. The method of claim 62, further comprising:
visually determining akinetic and viable tissue; and
determining a demarkation line between non-viable tissue and viable tissue of the left ventricle.

85. The method of claim 62, further comprising:
detecting electrical pulses from viable tissue; and
determining a demarkation line between non-viable tissue and viable tissue of the left ventricle.

86. The method of claim 62, further comprising excluding at least some of the non-viable tissue of the left ventricle.

87. The method of claim 62, further comprising:
determining a demarkation line between non-viable tissue and viable tissue of the left ventricle; and
excluding at least some of the non-viable tissue;
placing at least one suture along at least a portion of the demarkation line; and
pulling the suture such that the left ventricle is pulled around the shaper.

88. The method of claim 87, further comprising attaching a patch along at least a portion of one of the demarkation lines.

89. The method of claim 87, further comprising suturing a patch along at least a portion of one of the demarkation lines.

90. The method of claim 87, further comprising suturing a patch to an interior of the left ventricle.

91. The method of claim 87, further comprising excluding scar tissue from viable tissue of the left ventricle.

92. A shaping system, comprising:
a shaper positionable in a left ventricle of a human heart during use, wherein the shaper comprises a predetermined shape, wherein the predetermined shape acts as a pattern to reconstruct the left ventricle about the shaper during use, and wherein a first portion of the shaper has a first wall thickness;
wherein a second portion of the shaper comprises a second wall thickness greater than the first wall thickness, wherein the shaper is configured to inhibit perforation of the shaper during use, and wherein the second portion comprises a self sealing material.

93. The system of claim 92, wherein the shaper comprises an expandable balloon.

94. The system of claim 92, wherein the shaper comprises a predetermined contour.

95. The system of claim 92, wherein the shaper is configured to contain at least one fluid in at least a portion of the shaper.

96. The system of claim 92, wherein the shaper is configured to contain at least one shaper to the predetermined shape.

97. The system of claim 92, wherein the shaper is configured to inhibit expansion beyond a predetermined point.

98. The system of claim 92, wherein the shaper is configured to inhibit distortion of the predetermined shape when expanded.

99. The system of claim 92, wherein the shaper is expanded to the predetermined shape.

100. The system of claim 92, further comprising a tube coupled to the shaper, wherein the tube is configurable to convey a fluid to the shaper.

101. The system of claim 92, further comprising a tube coupled to the shaper, wherein the tube is configurable to convey a fluid to the shaper from a pressurized fluid reservoir.

102. The system of claim 92, further comprising a tube coupled to the shaper, wherein the tube is configurable to convey a fluid to the shaper from a pressurized fluid reservoir, and further comprising a valve coupled to the tube, wherein the valve is configurable to maintain a pressure of the fluid.

103. The system of claim 92, wherein the shaper has a short axis and a long axis.

104. The system of claim 92, wherein the shaper has a short axis and a long axis, and wherein the ratio of the short axis to the long axis is about 0.3 to about 0.7.

105. A shaping system, comprising:
a shaper positionable in a left ventricle of a human heart during use, wherein the shaper comprises a predetermined shape, wherein the predetermined shape acts as a pattern to reconstruct the left ventricle about the shaper during use, and wherein a first portion of the shaper has a first wall thickness;
wherein a second portion of the shaper comprises a second wall thickness greater than the first wall thickness, wherein the shaper is configured to inhibit perforation of the shaper during use, wherein the second portion comprises a self sealing material, and wherein the self sealing material comprises self sealing latex rubber.

106. The system of claim 105, wherein the shaper comprises an expandable balloon.

107. The system of claim 105, wherein the shaper comprises a predetermined contour.

108. The system of claim 105, wherein the shaper is configured to contain at least one fluid in at least a portion of the shaper.

109. The system of claim 105, wherein the shaper is configured to contain at least one fluid in at least a portion of the shaper, and wherein the fluid is configurable to expand the shaper to the predetermined shape.

110. The system of claim 105, wherein the shaper is configured to inhibit expansion beyond a predetermined point.

111. The system of claim 105, wherein the shaper is configured to inhibit distortion of the predetermined shape when expanded.

112. The system of claim 105, wherein the shaper is expanded to the predetermined shape.

113. The system of claim 105, further comprising a tube coupled to the shaper, wherein the tube is configurable to convey a fluid to the shaper.

114. The system of claim 105, further comprising a tube coupled to the shaper, wherein the tube is configurable to convey a fluid to the shaper from a pressurized fluid reservoir.

115. The system of claim 105, further comprising a tube coupled to the shaper, wherein the tube is configurable to convey a fluid to the shaper from a pressurized fluid reservoir, and further comprising a valve coupled to the tube, wherein the valve is configurable to maintain a pressure of the fluid.

116. The system of claim 105, wherein the shaper has a short axis and a long axis.

117. The system of claim 105, wherein the shaper has a short axis and a long axis, and wherein the ratio of the short axis to the long axis is about 0.3 to about 0.7.

118. A method for reshaping a left ventricle of a human heart, comprising:
  engaging a wall of the left ventricle of a beating heart to sense tactile feedback;
  determining a demarcation line between non-viable tissue and viable tissue of the left ventricle;
  positioning a shaper in the left ventricle, wherein the left ventricle has a first shape;
  using the shaper as a model to reshape at least a portion of the left ventricle such that the reshaped left ventricle has a second shape; and
  removing the shaper from the left ventricle.

119. The method of claim 118, wherein the second shape is substantially similar to the shape of an appropriate left ventricle of a heart.

120. The method of claim 118, wherein the first shape is the shape of an enlarged left ventricle of a heart.

121. The method of claim 118, wherein the first shape is substantially spherical.

122. The method of claim 118, wherein the first shape comprises a greater volume relative to the second shape.

123. The method of claim 118, wherein at least a portion of the second shape substantially corresponds to at least a portion of a size of the shaper.

124. The method of claim 118, wherein at least a portion of the second shape substantially corresponds to at least a portion of a shape of the shaper.

125. The method of claim 118, wherein at least a portion of the second shape substantially corresponds to at least a portion of a size of the shaper, and wherein at least a portion of the second shape substantially corresponds to at least a portion of a shape of the shaper.

126. The method of claim 118, wherein the shaper has a short axis and a long axis.

127. The method of claim 118, wherein the shaper has a short axis and a long axis, and wherein the ratio of the short axis to the long axis is about 0.3 to about 0.7.

128. The method of claim 118, wherein the shaper is substantially ellipsoid in shape.

129. The method of claim 118, wherein the shaper is substantially conical in shape.

130. The method of claim 118, wherein the shaper is substantially pear shaped.

131. The method of claim 118, wherein the shaper is substantially tear drop shaped.

132. The method of claim 118, wherein the reshaping comprises pressing at least a portion of the left ventricle against the shaper.

133. The method of claim 118, wherein the reshaping comprises using the firmness of the shaper to resist deformation of the shaper when at least a portion of the left ventricle is pressed against the shaper.

134. The method of claim 118, further comprising demarking between non-viable tissue and viable tissue of the left ventricle.

135. The method of claim 118, wherein the reshaping comprises pressing at least a portion of the left ventricle against the shaper and using the firmness of the shaper to resist deformation of the shaper when at least a portion of the left ventricle is pressed against the shaper.

136. The method of claim 118, further comprising demarking between non-viable tissue and viable tissue of the left ventricle, and wherein the reshaping comprises pressing at least a portion of the left ventricle against the shaper and using the firmness of the shaper to resist deformation of the shaper when at least a portion of the left ventricle is pressed against the shaper.

137. The method of claim 118, wherein the reshaping comprises pressing at least a portion of the left ventricle against the shaper and using the firmness of the shaper to resist deformation of the shaper when at least a portion of the left ventricle is pressed against the shaper, and further comprising attaching a patch to at least a portion of the left ventricle.

138. The method of claim 118, further comprising visually determining akinetic and viable tissue.

139. The method of claim 118, further comprising detecting electrical pulses from viable tissue.

140. The method of claim 118, further comprising excluding at least some of the non-viable tissue of the left ventricle.

141. The method of claim 118, further comprising:
  excluding at least some of the non-viable tissue;
  placing at least one suture along at least a portion of the demarcation line; and
  pulling the suture such that the left ventricle is pulled around the shaper.

142. The method of claim 141, further comprising attaching a patch along at least a portion of one of the demarcation lines.

143. The method of claim 141, further comprising suturing a patch along at least a portion of one of the demarcation lines.

144. The method of claim 141, further comprising suturing a patch to an interior of the left ventricle.

145. The method of claim 141, further comprising excluding scar tissue from viable tissue of the left ventricle.

* * * * *

UNITED STATES PATENT AND TRADEMARK OFFICE
CERTIFICATE OF CORRECTION

PATENT NO. : 6,994,093 B2
APPLICATION NO. : 09/864510
DATED : February 7, 2006
INVENTOR(S) : Murphy et al.

It is certified that error appears in the above-identified patent and that said Letters Patent is hereby corrected as shown below:

In the Claims:

Claim 52, col. 19, line 25, please delete "claim 50" and substitute therefor --"claim 51" --.

Claim 90, col. 21, line 37, please delete "claim 87" and substitute therefor --"claim 62" --.

Claim 91, col. 21, line 39, please delete "claim 87" and substitute therefor --"claim 62" --.

Claim 96, col. 21, line 61, please delete "shaper to the predetermined shape" and substitute therefor --"fluid in at least a portion of the shaper, and wherein the fluid is configurable to expand the shaper to the predetermined shape" --.

Claim 144, col. 24, line 48, please delete "claim 141" and substitute therefor --"claim 118" --.

Claim 145, col. 24, line 50, please delete "claim 141" and substitute therefor --"claim 118" --.

Signed and Sealed this

Fifth Day of June, 2007

JON W. DUDAS
*Director of the United States Patent and Trademark Office*